(12) United States Patent
Kopetzki et al.

(10) Patent No.: US 10,155,970 B2
(45) Date of Patent: Dec. 18, 2018

(54) USE OF AN AMINO ACID AUXOTROPHY CURED PROKARYOTIC STRAIN FOR THE RECOMBINANT PRODUCTION OF A POLYPEPTIDE

(71) Applicant: Hoffmann-La Roche Inc., Little Falls, NJ (US)

(72) Inventors: Erhard Kopetzki, Penzberg (DE); Christian Schantz, Penzberg (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 132 days.

(21) Appl. No.: 14/769,594

(22) PCT Filed: Feb. 19, 2014

(86) PCT No.: PCT/EP2014/053171
§ 371 (c)(1),
(2) Date: Aug. 21, 2015

(87) PCT Pub. No.: WO2014/128135
PCT Pub. Date: Aug. 28, 2014

(65) Prior Publication Data
US 2015/0376674 A1      Dec. 31, 2015

(30) Foreign Application Priority Data
Feb. 22, 2013  (EP) .................................... 13156288

(51) Int. Cl.
*C12P 21/00* (2006.01)
*C12P 21/02* (2006.01)

(52) U.S. Cl.
CPC .............. *C12P 21/00* (2013.01); *C12P 21/02* (2013.01)

(58) Field of Classification Search
CPC ........... C12N 15/70; C12P 21/00; C12P 21/02
See application file for complete search history.

(56) References Cited

U.S. PATENT DOCUMENTS
6,291,245 B1   9/2001   Kopetzki et al.

FOREIGN PATENT DOCUMENTS

| EP | 0 972 838 A1 | 1/2000 |
| JP | 2000-50888 | 2/2000 |
| WO | 2012/028526 A2 | 3/2012 |
| WO | 2012/028526 A3 | 3/2012 |

OTHER PUBLICATIONS

Bhattacharjee et al., "Ultraviolet-Induced Reversion to Prototrophy in Histidine-Requiring *Escherichia coli* B/r" Mutation Research 52:285-289 ( 1978).
Gardner et al., "Operator-Promoter Functions in the Threonine Operon of *Escherichia coli*" Journal of Bacteriology 124(1):161-166 (Oct. 1975).
Huang et al., "Industrial production of recombinant therapeutics in *Escherichia coli* and its recent advancements" J Ind Microbiol Biotechnol 39:383-399 ( 2012).
International Search Report and Written Opinion for International Patent Application No. PCT/EP2014/053171, dated Apr. 4, 2014, 13 pages.
Kada, "Studies on the mutability of *Escherichia coli* K12. I. Suppression and high spontaneous mutation in a threonine auxotroph." Mutation Res. 10:91-102 ( 1970).
Schmidt et al., "Conquering isoleucine auxotrophy of *Escherichia coli* BLR(DE3) to recombinantly produce spider silk proteins in minimal media" Biotechnol Lett 29:1741-1744 (2007).
Tanaka et al., "Induction of Mutation in *Escherichia coli* by Freeze-Drying" Applied and Environmental Microbiology 37(3):369-372 (Mar. 1979).
Vidal et al., "Development of an antibiotic-free plasmid selection system based on glycine auxotrophy for recombinant protein overproduction in *Escherichia coli*" Journal of Biotechnology 134:127-136 ( 2008).

*Primary Examiner* — Kagnew H Gebreyesus
(74) *Attorney, Agent, or Firm* — Steven Cui

(57) ABSTRACT

Herein is reported a method for producing a polypeptide in a prokaryotic cell, comprising the step of cultivating a prokaryotic cell comprising one or more nucleic acids encoding the polypeptide in a chemically defined minimal growth medium and recovering the polypeptide from the prokaryotic cell or the periplasm of the prokaryotic cell or from the medium, wherein the prokaryotic cell is an amino acid auxotrophy cured prokaryotic cell, wherein growth of the amino acid auxotrophy cured prokaryotic cell compared to the non-cured prokaryotic cell under the same cultivation conditions and in the same growth medium requires the supplementation of fewer amino acids to the growth medium, and wherein the chemically defined minimal growth medium is free of the amino acid corresponding to the auxotrophy that has been cured in the auxotrophy cured prokaryotic cell.

14 Claims, 13 Drawing Sheets
Specification includes a Sequence Listing.

Figure 3
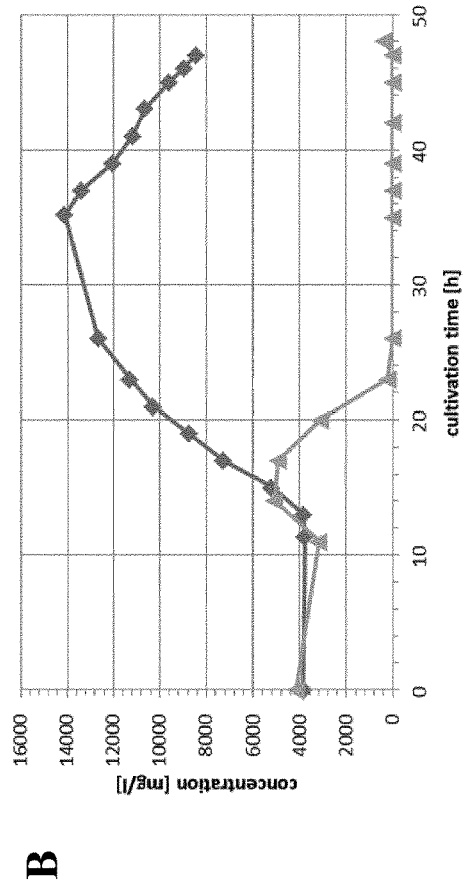
B
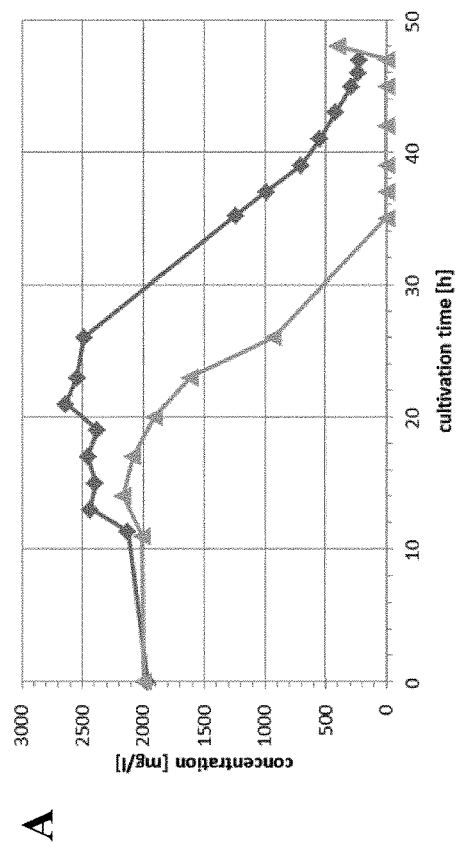
A

US 10,155,970 B2

USE OF AN AMINO ACID AUXOTROPHY CURED PROKARYOTIC STRAIN FOR THE RECOMBINANT PRODUCTION OF A POLYPEPTIDE

CROSS REFERENCE TO RELATED APPLICATIONS

This application is a 371 of International Application No. PCT/EP2014/053171, filed Feb. 19, 2014, claiming priority to Application No. EP13156288.6, filed, Feb. 22, 2013, the contents of which are incorporated herein by reference.

The current invention is in the field of recombinant polypeptide production. More precisely herein is reported a method for the recombinant production of a non-glycosylated polypeptide using an auxotrophy cured prokaryotic strain in a chemically defined minimal growth medium.

BACKGROUND OF THE INVENTION

In recent years the production of therapeutic polypeptides has steadily increased and it is likely that therapeutic polypeptides will become the biggest group of therapeutics available for the treatment of various diseases in the near future. The impact of therapeutic polypeptides emerges from their specificity, such as specific target recognition and/or binding function.

Cell cultures are used in fermentative processes to produce substances and in particular polypeptides. A distinction is made between processes in which the cell cultures are genetically unmodified and form their own metabolic products and processes in which the organisms are genetically modified in such a manner that they either produce a larger amount of their own substances such as polypeptides or produce foreign substances. The organisms producing the substances are supplied with a nutrient medium which guarantees the survival of the organisms and enables the production of the desired target compound. Numerous culture media are known for these purposes which enable an optimal cultivation of the specific host.

The use of a chemically defined minimal growth medium in the cultivation of a recombinant cell for the recombinant production of therapeutic polypeptides is advantageous. It enables easy development of downstream processing and purification of the produced therapeutic polypeptide, provides for a robust productions process due to minimized raw material differences and reduces costs of goods.

A chemically defined minimal growth medium does not comprise free amino acids and it is required to use prototrophic cell lines which have intact metabolic pathways to produce the required amino acids from the available components of the chemically defined minimal growth medium.

When, for example, E. coli is used as host cell line generally wild-type strains, such as MG1655, W3110 or BL21, are employed. These strains show good growth characteristics but inferior product titer.

Mutant prokaryotic strains, which have been obtained by non-directed mutagenesis and selection, show profound differences in their genomic DNA when compared to wild-type strains. The mutant strains have been selected based on the maximum product titer that can be obtained. As the mutant strains harbor a number of auxotrophies they cannot be used for cultivation in a chemically defined minimal growth medium. The mutant strains required the feeding of amino acids to complement their auxotrophies resulting in increased cultivation costs.

U.S. Pat. No. 5,932,439 reports *Escherichia coli* K-12 strains for production of recombinant proteins.

SUMMARY OF THE INVENTION

By curing an auxotrophic prokaryotic strain of one or more of its auxotrophies the auxotrophy cured strain can grow on a chemically defined minimal growth medium to which the substance corresponding to the auxotrophy that has been cured no further needs to be added. In case of expensive substances a reduction of the costs of goods can be achieved and a recombinant polypeptide can be produced more economically.

In addition to the restoration of the ability to grow on a chemically defined minimal growth medium in the absence of the substance corresponding to the auxotrophy that has been cured it has been found that the obtainable product titer can be maintained or even increased compared to the non-cured strain. It has furthermore been found that the obtainable product titer using an auxotrophy cured prokaryotic strain is higher than the product titer that can be obtained with a corresponding prototrophic wild-type strain.

Without being bound by this theory it is assumed that an amino acid auxotrophy cured prokaryotic strain as reported herein has a different metabolism and metabolic fluxes when compared to a corresponding prototrophic wild-type strain in which such a deletion and cure has not been performed. Thus, the inactivation and re-activation of certain enzymes within a prokaryotic strain has a detectable/pronounced effect on the entire metabolism of the strain, which can be seen, e.g. in the increased productivity of such a strain compared to a corresponding prototrophic wild-type strain.

One aspect as reported herein is an amino acid auxotrophy cured prokaryotic strain, characterized in that
    at least one deficiency in an essential amino acid metabolic pathway has been cured, and
    the strain can grow in chemically defined minimal growth medium that is free of the amino acid corresponding to the auxotrophy that has been cured in the auxotrophy cured prokaryotic strain.

In one embodiment the auxotrophy cured prokaryotic strain is an auxotrophy cured *E. coli* strain.

One aspect as reported herein is an amino acid auxotrophy cured prokaryotic cell, characterized in that
    at least one deficiency in an essential amino acid metabolic pathway has been cured, and
    the cell can grow in chemically defined minimal growth medium that is free of the amino acid corresponding to the auxotrophy that has been cured in the auxotrophy cured prokaryotic cell.

In one embodiment the auxotrophy cured prokaryotic cell is an auxotrophy cured *E. coli* cell.

The auxotrophy cured prokaryotic strain/cell as reported herein can be used in a method for the recombinant production of a therapeutic polypeptide wherein compared to the non-auxotrophy cured strain/cell the supplementation of at least one amino acid residue is not required.

One aspect as reported herein is a method for producing a polypeptide in a (recombinant) prokaryotic cell, comprising the following step:
    cultivating a (recombinant) prokaryotic cell, which has been obtained by introducing into the genome of a parent prokaryotic cell a nucleic acid curing an amino acid auxotrophy of the parent prokaryotic cell, comprising one or more nucleic acids encoding the polypeptide in a chemically defined minimal growth medium and recovering the polypeptide from the prokaryotic cell or the periplasm of the prokaryotic cell or from the medium.

One aspect as reported herein is a method for producing a polypeptide in a (recombinant) prokaryotic cell, comprising the following steps:

curing an prokaryotic cell that is auxotrophic for at least one amino acid from at least one amino acid auxotrophy, cultivating the amino acid auxotrophy cured (recombinant) prokaryotic cell comprising one or more nucleic acids encoding the polypeptide in a chemically defined minimal growth medium and recovering the polypeptide from the prokaryotic cell or the periplasm of the prokaryotic cell or from the medium.

One aspect as reported herein is a method for producing a polypeptide in a (recombinant) prokaryotic cell, comprising the following step:

cultivating a (recombinant) prokaryotic cell comprising one or more nucleic acids encoding the polypeptide in a chemically defined minimal growth medium and recovering the polypeptide from the prokaryotic cell or the periplasm of the prokaryotic cell or from the medium, wherein the (recombinant) prokaryotic cell is an amino acid auxotrophy cured prokaryotic cell.

In one embodiment of all methods for producing a polypeptide the auxotrophy cured prokaryotic cell has at least one further (non-cured) amino acid auxotrophy. This auxotrophy can be used for the selection of recombinants/transformants after the introduction of one or more nucleic acids encoding a polypeptide of interest (the polypeptide).

In one embodiment of all methods for producing a polypeptide the growth of the amino acid auxotrophy cured prokaryotic cell compared to the non-cured prokaryotic cell (parent cell) under the same cultivation conditions and in the same growth medium requires the supplementation of fewer amino acids to the growth medium.

In one embodiment of all methods for producing a polypeptide the chemically defined minimal growth medium is free of the amino acid corresponding to the auxotrophy that has been cured in the auxotrophy cured prokaryotic cell.

In one embodiment of all methods for producing a polypeptide the cultivation of the auxotrophy cured prokaryotic cell requires supplementation of one or two or three or four amino acids less to the growth medium than required for the cultivation of the non-auxotrophy cured prokaryotic cell (parent/parent cell).

In one embodiment of all methods for producing a polypeptide the amino acid corresponding to the auxotrophy that has been cured in the auxotrophy cured prokaryotic cell is not added during the cultivation.

In one embodiment of all methods for producing a polypeptide the cultivation is in the absence of the amino acid corresponding to the auxotrophy that has been cured in the auxotrophy cured prokaryotic cell.

In one embodiment of all methods for producing a polypeptide the prokaryotic cell is an *E. coli* cell.

In one embodiment of all methods for producing a polypeptide the polypeptide is a full length antibody chain, a single chain antibody, a single domain antibody, a scFv, a scFab, or a conjugate of one of the before with a non-antibody polypeptide.

In one embodiment of all methods for producing a polypeptide the polypeptide is a conjugate of a scFv or scFab with a cytotoxic agent.

One aspect as reported herein is the use of an amino acid auxotrophy cured prokaryotic strain for the (recombinant) production of a polypeptide.

In one embodiment
in the amino acid auxotrophy cured prokaryotic strain at least one deficiency in an essential amino acid metabolic pathway has been cured, and
the amino acid auxotrophy cured strain can grow in chemically defined minimal growth medium that is free of the amino acid corresponding to the auxotrophy that has been cured in the auxotrophy cured prokaryotic strain.

In one embodiment the auxotrophy cured prokaryotic strain is an auxotrophy cured *E. coli* strain.

In one embodiment the polypeptide is a full length antibody chain, a single chain antibody, a single domain antibody, a scFv, a scFab, or a conjugate of one of the before with a non-antibody polypeptide.

In one embodiment the polypeptide is a conjugate of a scFv or scFab with a cytotoxic agent.

In one embodiment of all aspects the auxotrophy cured prokaryotic strain is a non-lysogenic strain. A lysogenic strain is infected with a temporal bacteriophage, i.e. a non-lysogenic strain is free of bacteriophages.

In one embodiment of all aspects the cure is a directed cure targeting only the amino acid auxotrophy.

In one embodiment of all aspects the cure is the introduction of one or more enzymes required for the synthesis of the auxotrophic amino acid.

In one embodiment of all aspects the prokaryotic strain has the genotype thi-1, ΔompT, ΔpyrF.

DETAILED DESCRIPTION OF THE INVENTION

One aim in the development of large scale recombinant polypeptide production processes is the reduction of the required amount, i.e. the consumption, of medium components during the cultivation. Especially the reduction of the consumption of expensive medium components, such as amino acids, is advantageous in view of costs of goods.

This aim has been achieved by curing an amino acid auxotrophic strain from at least one, some, or all of its amino acids auxotrophies in order to avoid feeding of expensive amino acids and therewith to reduce the costs of the recombinant production of a polypeptide of interest. Additionally a chemical defined medium can be used which results in an improved process stability and facilitates downstream processing (DSP).

Thus, herein is reported a method for the recombinant production of a non-glycosylated polypeptide using an auxotrophy cured prokaryotic strain in a chemically defined minimal growth medium.

It has been found that by curing an auxotrophic prokaryotic strain of one or more of its auxotrophies the auxotrophy cured strain can grow on a chemically defined minimal growth medium to which the substance corresponding to the auxotrophy that has been cured no further needs to be added. In case of expensive substances, such as e.g. amino acids, a reduction of the costs of goods can be achieved and a recombinant polypeptide can be produced more economically.

In addition to the restoration of the ability to grow on a chemically defined minimal growth medium in the absence of the substance corresponding to the auxotrophy that has been cured it has been found that the obtainable product titer can be maintained or even increased. It has furthermore been found that the obtainable product titer using an auxotrophy cured prokaryotic strain is higher than the product titer that can be obtained with a corresponding prototrophic wild-type strain.

One aspect as reported herein is a method for producing a polypeptide in a prokaryotic cell, comprising the following step:
cultivating a prokaryotic cell, which has been obtained by introducing into the genome of a parent prokaryotic cell a nucleic acid curing an amino acid auxotrophy of the parent prokaryotic cell, comprising one or more nucleic acids encoding the polypeptide in a chemically defined minimal growth medium and recovering the polypeptide from the prokaryotic cell or the periplasm of the prokaryotic cell or from the medium.

One aspect as reported herein is a method for producing a polypeptide in a prokaryotic cell, comprising the following steps:
curing an prokaryotic cell that is auxotrophic for at least one amino acid from at least one amino acid auxotrophy,
cultivating the amino acid auxotrophy cured prokaryotic cell comprising one or more nucleic acids encoding the polypeptide in a chemically defined minimal growth medium and recovering the polypeptide from the prokaryotic cell or the periplasm of the prokaryotic cell or from the medium.

One aspect as reported herein is a method for producing a polypeptide in a (recombinant) prokaryotic cell, comprising the following step:
cultivating a (recombinant) prokaryotic cell comprising one or more nucleic acids encoding the polypeptide in a chemically defined minimal growth medium and recovering the polypeptide from the prokaryotic cell or the periplasm of the prokaryotic cell or from the medium,
wherein the (recombinant) prokaryotic cell is an amino acid auxotrophy cured prokaryotic cell,
wherein growth of the amino acid auxotrophy cured prokaryotic cell compared to the non-cured prokaryotic cell (parent cell) under the same cultivation conditions and in the same growth medium requires the supplementation of fewer amino acids to the growth medium, and
wherein the chemically defined minimal growth medium is free of the amino acid corresponding to the auxotrophy that has been cured in the auxotrophy cured prokaryotic cell.

An "amino acid auxotrophic prokaryotic cell" is a prokaryotic cell that cannot synthesize an essential amino acid e.g. due to a mutation or deletion within a gene locus comprising the structural gene encoding the proteins of the corresponding biosynthetic pathway. Without the addition of the respective amino acid to the cultivation medium the cell cannot proliferate. The auxotrophy can be for any amino acid. The prokaryotic cell can also be auxotrophic for more than one amino acid. Thus, in one embodiment the amino acid auxotrophic prokaryotic cell is auxotrophic for at least two amino acids. In another embodiment the amino acid auxotrophic prokaryotic cell is auxotrophic for at least two, at least three, at least four, at least five amino acids. In a further embodiment the amino acid auxotrophic prokaryotic cell is auxotrophic for at least 2 and up to 5, or up to 10, or up to 15 amino acids. In another embodiment the amino acid auxotrophic prokaryotic cell is auxotrophic for two to five amino acids, or two to three amino acids, or for two amino acids, or for three amino acids, or for four amino acids. In one embodiment the (amino acid) auxotrophy cured cell has at least one amino acid auxotrophy, or at least two amino acid auxotrophies, or at least three amino acid auxotrophies, or from one to three amino acid auxotrophies, or two amino acid auxotrophies.

The amino acid auxotrophic prokaryotic cell is in one embodiment a bacterial cell.

In one embodiment the cell is an *Escherichia* cell, or a *Bacillus* cell, or a *Lactobacillus* cell, or a *Corynebacterium* cell, or a Yeast cell (*Saccharomyces, Candida,* or *Pichia*). In a further embodiment the cell is an *Escherichia coli* cell, or a *Bacillus subtilis* cell, or a *Lactobacillus acidophilus* cell, or a *Corynebacterium glutamicum* cell, or a *Pichia pastoris* yeast cell.

Prokaryotic cells that can be used in the method as reported herein can comprise one or more amino acid auxotrophies. For example, *E. coli* cells deficient in the Leucine biosynthetic pathway can be selected from the LeuB6 deficient cells 13-6, χ148, χ156, χ2224, χ462, χ463, χ474, χ478, χ515, χ65, χ697, χ760, 2000 k MSE248, 342-167, 342MG, 679-680, A586, A592, A593, AA100, AA7852, AA787, AB1102, AB1111, AB1115, AB1122, AB1129, AB113, AB1132, AB1133, AB114, AB1157, AB1157-D, AB1314, AB1330, AB1331, AB1881, AB1884, AB1885, AB188, CP78, CP79, CR34 Thy-, CR34 Thy-SR, CR34/308, CR34/313, CR34/399, CR34/43, CR34/454, CR34/500, CR34/7a, CS130, CS312, CS419, CS425, CS426, CS460, CS471, CS472, CS50, CS81, CS85, CSR06, CSR603, CSR603/pDR1996, CT28-3b, DA10, DA11, DB1161, DB1257, DE1878, DE1882, DE2345, DF225, DF41, JRG94, JS10 C600r-m-, T6R, P678SSR pro-, PA20SR, PA200 SR, PA201 SR, PA214SRT6R, PA265 SR, PA309, PDE70, PA340, PA340/T6, PA360, PA414, PAM161, PAM162, PAM163, PAM164, PAM660, PAT84, PB349, PB69, PC1, PC2, PC3, PC5, PC6, PC8, PJ1, PJ2, PJ3, PJ4, PJ5, PJ C600 (=CRSR), W208 SR AzR, W2660, LAM-, W945his, WA2127, WA2379, WA2548, WA2552, WA2574, WA2899, WA921, WA946, WA960, Y10, Y46, Y53, Y70, YYC100.

In one embodiment the prokaryotic cell is an *E. coli* K12 cell or an *E. coli* B cell.

The term "growth" refers to the change in viable cell density in a cultivation. This change can be a change over time. The viable cell density can be determined by determining the optical density at 578 nm.

In one embodiment the growth is the increase of viable cell density during a time period. In one embodiment the time period is the time period of 0 to 30 hours of the cultivation after inoculation.

The term "same" denotes that a second value is within +/−20% of a first value. With respect to cultivation conditions the term "same" refers to cultivation time, cultivation volume, cultivation temperature, seeding cell density, aeration rate, pH value, stirrer speed, feed rate (if applicable), etc. With respect to the cultivation medium the term "same" denotes that a second medium compared to a first medium differs in at most 5 components (differ=presence or absence).

In one embodiment the same cultivation conditions are the identical cultivation conditions. In one embodiment the same cultivation medium is the identical cultivation medium.

Methods for cultivating a prokaryotic cell and also for cultivating an amino acid auxotrophic prokaryotic cell are known to a person of skill in the art (see e.g. Riesenberg, D., et al., Curr. Opin. Biotechnol. 2 (1991) 380-384).

The cultivating can be with any method. In one embodiment the cultivating is a batch cultivating, a fed-batch cultivating, a perfusion cultivating, a semi-continuous cultivating, or a cultivating with full or partial cell retention.

In one embodiment the cultivating is a high cell density cultivating. The term "high cell density cultivating" denotes a cultivating method wherein the dry cell weight of the cultivated prokaryotic cell is at one point in the cultivating at least 10 g/L. In one embodiment the dry cell weight is at one point in the cultivating at least 20 g/L, or at least 50 g/L, or at least 100 g/L, or more than 100 g/L. In order to reach such a high cell density state the volume of feed and/or adjustment solutions added during the cultivating has to be as small as possible. Methods for the determination of dry cell weight are reported e.g. in Riesenberg, D., et al., Appl. Microbiol. Biotechnol. 34 (1990) 77-82.

The nutrients in the provided medium will be metabolized during the cultivation and have to be replenished in order to avoid a limitation.

| experiment no. | prokaryotic strain/expression plasmid | chemically defined minimal medium+ | product titer | see example |
|---|---|---|---|---|
| 1 | CSPZ-2/5816 | Leu, Pro | 16.1 g/L | 3 |
| 2 | CSPZ-6/5816 | Leu, Pro | 19.2 g/L | 3 |
| 5 | CSPZ-6/5816 | — | 20.8 g/L | 5 |
| 6 | MG1655 (ΔpyrF)/5816 | — | 10.9 g/L | 5 |

From the comparison of experiment no. 1 with experiment no. 2 it can be seen that with the auxotrophy cured strain CSPZ-6 a higher titer can be achieved than with its parent strain CSPZ-2 under the same cultivation conditions, i.e. the auxotrophy cured strain has an increased productivity (volumetric productivity, time-space-yield).

From the comparison of experiment no. 2 with experiment no. 5 it can be seen that the auxotrophy cured strain CSPZ-6 does not require the addition of the amino acids proline and leucine for recombinant production. A comparable or even slightly increased product titer can be achieved in the absence of proline and leucine.

From the comparison of experiment no. 5 with experiment no. 6 it can be seen that with the auxotrophy cured strain CSPZ-6 a higher titer can be achieved than with a corresponding wild-type strain (MG1655 (ΔpyrF)) under the same cultivation conditions.

| experiment no. | prokaryotic strain/expression plasmid | chemically defined minimal medium+ | product titer | see example |
|---|---|---|---|---|
| 7 | CSPZ-6/5830 | — | 22.6 g/L | 6 |
| 8 | 66C5/5830 | — | 2.3 g/L | 6 |
| 9 | 66C5/5830 | — | 6.9 g/L | 6 (elevated temperature) |

The product titer obtainable with the auxotrophy cured strain CSPZ-6 has also been compared with the product titer obtainable with another corresponding wild-type strain W3110 (66C5=W3110 ΔpyrF).

From the comparison of experiment no. 7 with experiment no. 8 it can be seen that with the auxotrophy cured strain CSPZ-6 a higher titer can be achieved than with a corresponding wild-type strain (W3110) under the same cultivation conditions.

From the comparison of experiment no. 7 with experiment no. 9 it can be seen that with the auxotrophy cured strain CSPZ-6 a higher titer can be achieved than with a corresponding wild-type strain (W3110) even if improved cultivation conditions (elevated temperature) are used for the wild-type strain but not for the auxotrophy cured strain.

| experiment no. | prokaryotic strain/expression plasmid | chemically defined minimal medium+ | product titer | see example |
|---|---|---|---|---|
| 10 | CSPZ-6/5836 | — | 33.8 g/L | 7 |
| 11 | CSPZ-14/5836 | — | 9.6 g/L | 7 |

The product titer obtainable with the auxotrophy cured strain CSPZ-6 has also been compared with the product titer obtainable with another corresponding wild-type strain BL-21 (CSPZ-14=BL21 ΔpyrF).

From the comparison of experiment no. 10 with experiment no. 11 it can be seen that with the auxotrophy cured strain CSPZ-6 a higher titer can be achieved than with a corresponding wild-type strain (BL-21) under the same cultivation conditions.

One aspect as reported herein is an amino acid auxotrophy cured prokaryotic strain, characterized in that
    at least one deficiency in an essential amino acid metabolic pathway has been cured,
    the strain can grow in chemically defined minimal growth medium that is free of the amino acid corresponding to the auxotrophy that has been cured in the auxotrophy cured prokaryotic strain, and
    the productivity of the auxotrophy cured strain is improved compared to the productivity of the parental non-auxotrophy cured strain as well as compared to corresponding wild-type strains (corresponding genotype).

In one embodiment the auxotrophy cured prokaryotic strain is an auxotrophy cured E. coli strain.

One aspect as reported herein is an amino acid auxotrophy cured prokaryotic cell, characterized in that
    at least one deficiency in an essential amino acid metabolic pathway has been cured, and
    the cell can grow in chemically defined minimal growth medium that is free of the amino acid corresponding to the auxotrophy that has been cured in the auxotrophy cured prokaryotic cell.

In one embodiment the auxotrophy cured prokaryotic cell is an auxotrophy cured E. coli cell.

The auxotrophy cured prokaryotic strain/cell as reported herein can be used in a method for the recombinant production of a therapeutic polypeptide wherein compared to the non-auxotrophy cured strain/cell the supplementation of at least one amino acid residue is not required.

One aspect as reported herein is a method for producing a polypeptide in a (recombinant) prokaryotic cell, comprising the following step:
    cultivating a (recombinant) prokaryotic cell comprising one or more nucleic acids encoding the polypeptide in a chemically defined minimal growth medium and recovering the polypeptide from the prokaryotic cell or the periplasm of the prokaryotic cell or from the medium,
wherein the (recombinant) prokaryotic cell is an amino acid auxotrophy cured prokaryotic cell.

In one embodiment the growth of the amino acid auxotrophy cured prokaryotic cell compared to the non-cured prokaryotic cell (parent cell) under the same cultivation conditions and in the same growth medium requires the supplementation of fewer amino acids to the growth medium.

In one embodiment the chemically defined minimal growth medium is free of the amino acid corresponding to the auxotrophy that has been cured in the auxotrophy cured prokaryotic cell.

In one embodiment the cultivation of the auxotrophy cured prokaryotic cell requires supplementation of one or two or three or four amino acids less to the growth medium than required for the cultivation of the non-auxotrophy cured prokaryotic cell (parent cell).

In one embodiment the auxotrophy cured prokaryotic cell has at least one further (non-cured) amino acid auxotrophy.

In one embodiment the amino acid corresponding to the auxotrophy that has been cured in the auxotrophy cured prokaryotic cell is not added during the cultivation.

In one embodiment the cultivation is in the absence of the amino acid corresponding to the auxotrophy that has been cured in the auxotrophy cured prokaryotic cell.

In one embodiment the prokaryotic cell is an *E. coli* cell.

In one embodiment the polypeptide is a full length antibody chain, a single chain antibody, a single domain antibody, a scFv, a scFab, or a conjugate of one of the before with a non-antibody polypeptide.

In one embodiment polypeptide is a conjugate of a scFv or scFab with a cytotoxic agent.

In one embodiment the viable cell density at 30 hours after inoculation of the cultivation is higher in the cultivation of the auxotrophy cured strain than in the cultivation of the non-cured prokaryotic cell.

One aspect as reported herein is the use of an amino acid auxotrophy cured prokaryotic strain for the (recombinant) production of a polypeptide.

In one embodiment
  in the amino acid auxotrophy cured prokaryotic strain at least one deficiency in an essential amino acid metabolic pathway has been cured, and
  the amino acid auxotrophy cured strain can grow in chemically defined minimal growth medium that is free of the amino acid corresponding to the auxotrophy that has been cured in the auxotrophy cured prokaryotic strain.

In one embodiment the auxotrophy cured prokaryotic strain is an auxotrophy cured *E. coli* strain.

In one embodiment the polypeptide is a full length antibody chain, a single chain antibody, a single domain antibody, a scFv, a scFab, or a conjugate of one of the before with a non-antibody polypeptide.

In one embodiment the polypeptide is a conjugate of a scFv or scFab with a cytotoxic agent.

In one embodiment the method for producing a polypeptide in a prokaryotic cell, comprises the following step:
  cultivating a prokaryotic cell comprising one or more nucleic acids encoding the polypeptide in a chemically defined minimal growth medium and recovering the polypeptide from the prokaryotic cell or the periplasm of the prokaryotic cell or from the medium,
wherein the prokaryotic cell is an amino acid auxotrophy cured prokaryotic cell,
wherein growth of the amino acid auxotrophy cured prokaryotic cell compared to the non-cured prokaryotic cell under the same cultivation conditions and in the same growth medium requires the supplementation of fewer amino acids to the growth medium, and
wherein the chemically defined minimal growth medium is free of the amino acid corresponding to the auxotrophy that has been cured in the auxotrophy cured prokaryotic cell.

Specific Embodiments

1. An amino acid auxotrophy cured prokaryotic strain, characterized in that
    at least one deficiency in an essential amino acid metabolic pathway has been cured, and
    the strain can grow in chemically defined minimal growth medium that is free of the amino acid corresponding to the auxotrophy that has been cured in the auxotrophy cured prokaryotic strain.

2. The strain according to item 1, characterized in that the auxotrophy cured prokaryotic strain is an auxotrophy cured *E. coli* strain.

3. An amino acid auxotrophy cured prokaryotic cell, characterized in that
    at least one deficiency in an essential amino acid metabolic pathway has been cured, and
    the cell can grow in chemically defined minimal growth medium that is free of the amino acid corresponding to the auxotrophy that has been cured in the auxotrophy cured prokaryotic cell.

4. The strain according to item 3, characterized in that the auxotrophy cured prokaryotic cell is an auxotrophy cured *E. coli* cell.

5. A method for producing a polypeptide in a (recombinant) prokaryotic cell, comprising the following step:
    cultivating a (recombinant) prokaryotic cell, which has been obtained by introducing into the genome of a parent prokaryotic cell a nucleic acid curing an amino acid auxotrophy of the parent prokaryotic cell, comprising one or more nucleic acids encoding the polypeptide in a chemically defined minimal growth medium and recovering the polypeptide from the prokaryotic cell or the periplasm of the prokaryotic cell or from the medium.

6. A method for producing a polypeptide in a (recombinant) prokaryotic cell, comprising the following steps:
    curing an prokaryotic cell that is auxotrophic for at least one amino acid from at least one amino acid auxotrophy,
    cultivating the amino acid auxotrophy cured (recombinant) prokaryotic cell comprising one or more nucleic acids encoding the polypeptide in a chemically defined minimal growth medium and recovering the polypeptide from the prokaryotic cell or the periplasm of the prokaryotic cell or from the medium.

7. A method for producing a polypeptide in a (recombinant) prokaryotic cell, comprising the following step:
    cultivating a (recombinant) prokaryotic cell comprising one or more nucleic acids encoding the polypeptide in a chemically defined minimal growth medium and recovering the polypeptide from the prokaryotic cell or the periplasm of the prokaryotic cell or from the medium,
    wherein the (recombinant) prokaryotic cell is an amino acid auxotrophy cured prokaryotic cell.

8. The method according to any one of items 5 to 7, characterized in that the auxotrophy cured prokaryotic cell has at least one further (non-cured) amino acid auxotrophy.

9. The method according to any one of items 5 to 8, characterized in that the growth of the amino acid auxotrophy cured prokaryotic cell compared to the non-cured prokaryotic cell (parent cell) under the same cultivation conditions and in the same growth medium requires the supplementation of fewer amino acids to the growth medium.
10. The method according to any one of items 5 to 9, characterized in that the chemically defined minimal growth medium is free of the amino acid corresponding to the auxotrophy that has been cured in the auxotrophy cured prokaryotic cell.
11. The method according to any one of items 5 to 10, characterized in that the cultivation of the auxotrophy cured prokaryotic cell requires supplementation of one or two or three or four amino acids less to the growth medium than required for the cultivation of the non-auxotrophy cured prokaryotic cell (parent/parent cell).
12. The method according to any one of items 5 to 11, characterized in that the amino acid corresponding to the auxotrophy that has been cured in the auxotrophy cured prokaryotic cell is not added during the cultivation.
13. The method according to any one of items 5 to 12, characterized in that the cultivation is in the absence of the amino acid corresponding to the auxotrophy that has been cured in the auxotrophy cured prokaryotic cell.
14. The method according to any one of items 5 to 13, characterized in that the prokaryotic cell is an *E. coli* cell.
15. The method according to any one of items 5 to 14, characterized in that the polypeptide is a full length antibody chain, a single chain antibody, a single domain antibody, a scFv, a scFab, or a conjugate of one of the before with a non-antibody polypeptide.
16. The method according to any one of items 5 to 15, characterized in that the polypeptide is a conjugate of a scFv or scFab with a cytotoxic agent.
17. Use of an amino acid auxotrophy cured prokaryotic strain for the (recombinant) production of a polypeptide.
18. The use according to item 17, characterized in that
    in the amino acid auxotrophy cured prokaryotic strain at least one deficiency in an essential amino acid metabolic pathway has been cured, and
    the amino acid auxotrophy cured strain can grow in chemically defined minimal growth medium that is free of the amino acid corresponding to the auxotrophy that has been cured in the auxotrophy cured prokaryotic strain.
19. The strain or method or use according to any one of items 1 to 18, characterized in that the auxotrophy cured prokaryotic strain is an auxotrophy cured *E. coli* strain.
20. The strain or method or use according to any one of items 1 to 19, characterized in that the polypeptide is a full length antibody chain, a single chain antibody, a single domain antibody, a scFv, a scFab, or a conjugate of one of the before with a non-antibody polypeptide.
21. The strain or method or use according to any one of items 1 to 20, characterized in that the polypeptide is a conjugate of a scFv or scFab with a cytotoxic agent.
22. The strain or method or use according to any one of items 1 to 21, characterized in that the auxotrophy cured prokaryotic strain is a non-lysogenic strain.
23. The strain or method or use according to any one of items 1 to 22, characterized in that the cure is a directed cure targeting only the amino acid auxotrophy.
24. The strain or method or use according to any one of items 1 to 23, characterized in that the cure is the introduction of one or more enzymes required for the synthesis of the auxotrophic amino acid.
25. The strain or method or use according to any one of items 1 to 24, characterized in that the prokaryotic strain has the genotype thi-1, ΔompT, ΔpyrF.

The following examples, sequences and figures are provided to aid the understanding of the present invention, the true scope of which is set forth in the appended claims. It is understood that modifications can be made in the procedures set forth without departing from the spirit of the invention.

LIST OF SEQUENCES

SEQ ID NO: 01 Human interferon derived sequence.
SEQ ID NO: 02 Hexa-histidine affinity tag.
SEQ ID NO: 03 IgA protease cleavage site.
SEQ ID NO: 04 Tetranectin apolipoprotein A-I fusion polypeptide amino acid sequence.
SEQ ID NO: 05 N-terminal extended Tetranectin apolipoprotein A-I fusion polypeptide amino acid sequence obtained after IgA protease cleavage.
SEQ ID NO: 06 Tetranectin apolipoprotein A-I fusion polypeptide amino acid sequence without affinity tag and IgA protease cleavage (N-terminal shortened fusion polypeptide).

DESCRIPTION OF THE FIGURES

FIG. 3 A: Trend plot of the L-leucine concentration (CSPZ-2: diamonds; CSPZ-6: triangles).
    B: Trend plot of the L-proline concentration (CSPZ-2: diamonds; CSPZ-6: triangles).

EXAMPLES

Figure 1:
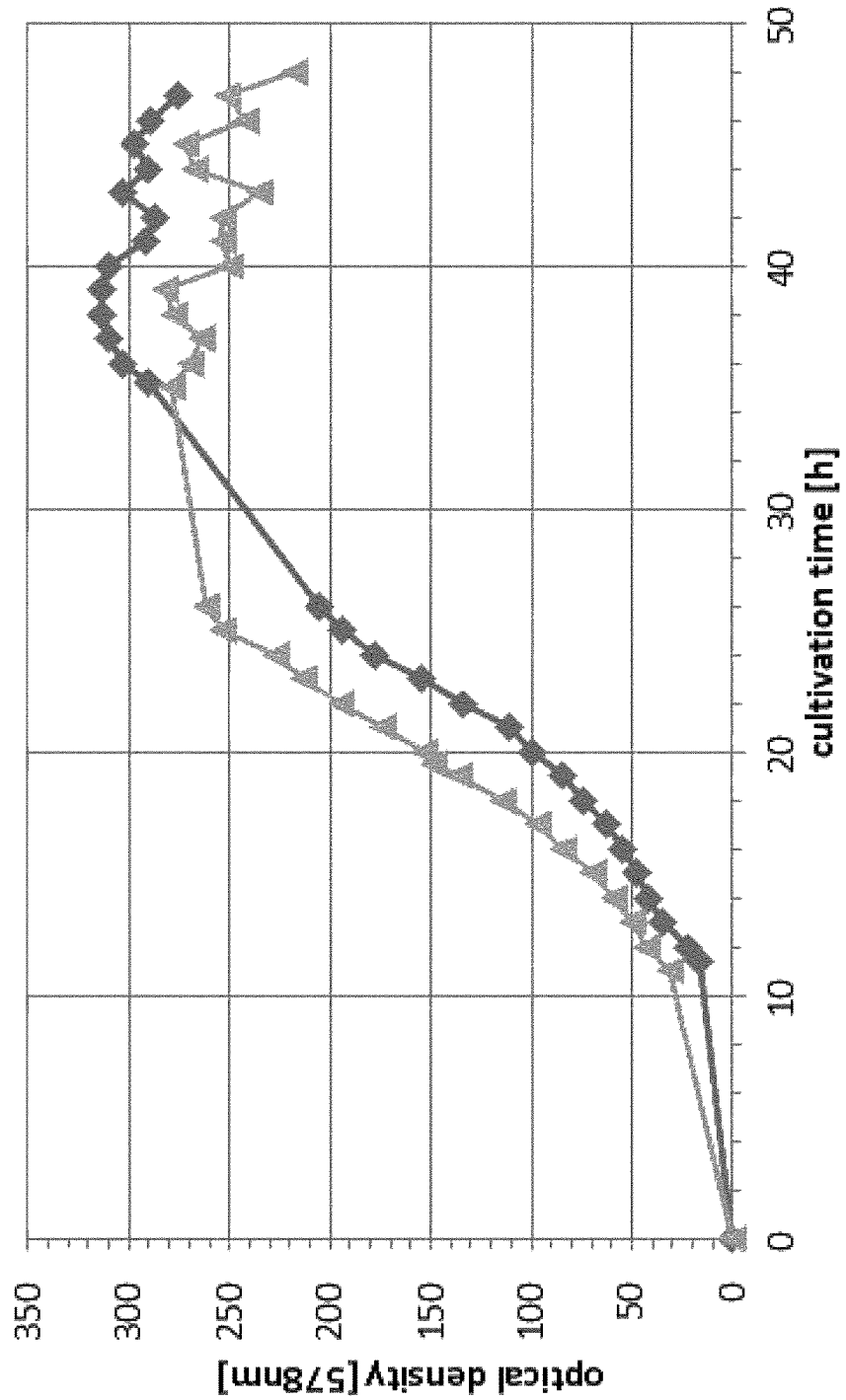
FIG. 1 Growth comparison of parental strain CSPZ-2 (diamonds) and auxotrophy cured strain CSPZ-6 (triangles).

Materials and Methods
Recombinant DNA Technique:

Standard methods were used to manipulate DNA as described in Sambrook, J., et al., Molecular cloning: A laboratory manual; Cold Spring Harbor Laboratory Press, Cold Spring Harbor, N. Y., 1989. The molecular biological reagents were used according to the manufacturer's instructions.

Example 1

Cure of Auxotrophy

The *E. coli* K12 strain CSPZ-2 (leuB, proC, trpE, thi-1, ΔpyrF) was cured from its genetic defects in the genes leuB, proC, proBA and trpE. This was done by using a method for directed genetic engineering of *E. coli* chromosomal genes (Gene Bridges, Heidelberg, Germany; http://www.genebridges.com; see e.g. WO 99/29837, WO 01/04288, U.S. Pat. No. 6,355,412). In detail the following stepwise changes were made:
Repair of leuB Locus:

The *E. coli* CSPZ-2 has a TCG to TTG point mutation in the locus leuB which results in a Serine to Leucine amino acid exchange at Position 286 in the corresponding 3-isopropylmalate dehydrogenase making this enzyme defective. The strain is therefore not able to grow on cultivation medium not supplemented with L-Leucine. With an oligonucleotide encoding the wild-type Ser286 with flanking sequences the genomic mutation in strain CSPZ-2 was exchanged to generate the cured strain CSPZ-3 (CSPZ-2 leuB+) which can grow on M9 medium plates supplemented with L-Proline but does not require L-Leucine.
Repair of proC (b0386) and proBA (b0242 and b0243) Loci:

The strain CSPZ-3 still requires the supplementation of Proline to grow on M9 minimal medium. A PCR-amplification of the proC locus resulted in an approx. 2.4 kb fragment. For *E. coli* K12 (wild-type strain) a 1,024 bp fragment was expected (Blattner, F. R., et al., Science 277 (1997) 1453-1474). Sequencing of the PCR product revealed the disruption of the proC locus by IS186 (1,335 bp) transposition into the genome. The proBA locus was characterized by PCR, but the amplification failed indicating the absence of the proBA operon.

A PCR product amplified from *E. coli* strain MG1655 genomic DNA was used for Red/ET recombination to cure the deficiency in the proC locus.

In a consecutive step the proBA operon was inserted via Red/ET recombination into the infA-serW intergenic region of the genome to restore prototrophic phenotype in CSPZ-4. The integration was verified by PCR amplifying and sequencing of the integration site and by plating on M9 minimal medium agar plates. The Proline prototrophic, auxotrophy cured strain was named CSPZ-5.
Repair of the trpE (b1264) Locus:

DNA sequencing of the trpE locus of the parental strain CSPZ-2 revealed the deletion of 9 nucleotides resulting in the loss of Glu139, Glu 140 and Arg141. This mutation does not lead to a Tryptophan auxotrophic phenotype but may affect enzyme activity and lead to reduced growth. Therefor the mutated trpE locus was exchanged by the wild-type locus via Red/ET recombination. Successful restoration of the trpE gene was confirmed by sequencing and the resulting strain was named CSPZ-6.

Example 2

Making of the Expression Plasmids
Tetranectin-apolipoprotein A-I Fusion Polypeptide The tetranectin-apolipoprotein A-I fusion polypeptide was prepared by recombinant means. The amino acid sequence of the expressed fusion polypeptide in N- to C-terminal direction is as follows:
  the amino acid methionine (M),
  a fragment of an interferon sequence that has the amino acid sequence of CDLPQTHSL (SEQ ID NO: 01),
  a GS linker,
  a hexa-histidine tag that has the amino acid sequence of HHHHHH (SEQ ID NO: 02),
  a GS linker,
  an IgA protease cleavage site that has the amino acid sequence of VVAPPAP (SEQ ID NO: 03), and
  a tetranectin-apolipoprotein A-I that has the amino acid sequence of SEQ ID NO: 04.

The tetranectin-apolipoprotein A-I fusion polypeptides as described above are precursor polypeptides from which the tetranectin-apolipoprotein A-I fusion polypeptides was released by enzymatic cleavage in vitro using IgA protease.

The precursor polypeptide encoding fusion gene was assembled with known recombinant methods and techniques by connection of appropriate nucleic acid segments. Nucleic acid sequences made by chemical synthesis were verified by DNA sequencing. The expression plasmid for the production of tetranectin-apolipoprotein A-I was prepared as follows.
Making of the *E. coli* Expression Plasmids
a) Plasmid 5816

Plasmid 4980 (4980-pBRori-URA3-LACI-SAC) is an expression plasmid for the expression of core-streptavidin in *E. coli*. It was generated by ligation of the 3142 bp long EcoRI/CelII-vector fragment derived from plasmid 1966 (1966-pBRori-URA3-LACI-T-repeat; reported in EP-B 1 422 237) with a 435 bp long core-streptavidin encoding EcoRI/CelII-fragment.

The core-streptavidin *E. coli* expression plasmid comprises the following elements:
  the origin of replication from vector pBR322 for replication in *E. coli* (corresponding to by position 2517-3160 according to Sutcliffe, G., et al., Quant. Biol. 43 (1979) 77-90),
  the URA3 gene of *Saccharomyces cerevisiae* coding for orotidine 5'-phosphate decarboxylase (Rose, M. et al. Gene 29 (1984) 113-124) which allows plasmid selection by complementation of *E. coli* pyrF mutant strains (uracil auxotrophy),
  the core-streptavidin expression cassette comprising
    the T5 hybrid promoter (T5-PN25/03/04 hybrid promoter according to Bujard, H., et al., Methods Enzymol. 155 (1987) 416-433 and Stueber, D., et al., Immunol. Methods IV (1990) 121-152) including a synthetic ribosomal binding site according to Stueber, D., et al. (see before),
    the core-streptavidin gene,
    two bacteriophage-derived transcription terminators, the λ-T0 terminator (Schwarz, E., et al., Nature 272 (1978) 410-414) and the fd-terminator (Beck E. and Zink, B. Gene 1-3 (1981) 35-58),
  the lad repressor gene from *E. coli* (Farabaugh P. J. Nature 274 (1978) 765-769).

The final expression plasmid 5816 for the expression of the tetranectin-apolipoprotein A-I precursor polypeptide was prepared by excising the core-streptavidin structural gene from plasmid 4980 using the singular flanking EcoRI and CelII restriction endonuclease cleavage site and inserting the EcoRI/CelII restriction site flanked nucleic acid encoding the precursor polypeptide into the 3142 bp long EcoRI/CelII-4980 vector fragment.

b) Plasmid 5830

Plasmid 5830 is identical to plasmid 5816 except that the codons encoding the tripeptide QKK are changed from caa aaa aag (plasmid 5816) to cag aag (plasmid 5830).

c) Plasmid 5836

The encoding fusion gene for expression of a shortened tetranectin-apolipoprotein A-I fusion protein is assembled with known recombinant methods and techniques by connection of appropriate nucleic acid segments. Nucleic acid sequences made by chemical synthesis are verified by DNA sequencing. The expression plasmid for the production of the fusion protein of SEQ ID NO: 06 can be prepared as follows:

Plasmid 4980 (4980-pBRori-URA3-LACI-SAC) is an expression plasmid for the expression of core-streptavidin in *E. coli*. It was generated by ligation of the 3142 bp long EcoRI/CelII-vector fragment derived from plasmid 1966 (1966-pBRori-URA3-LACI-T-repeat; reported in EP-B 1 422 237) with a 435 bp long core-streptavidin encoding EcoRI/CelII-fragment.

The core-streptavidin *E. coli* expression plasmid comprises the following elements:

- the origin of replication from vector pBR322 for replication in *E. coli* (corresponding to by position 2517-3160 according to Sutcliffe, G., et al., Quant. Biol. 43 (1979) 77-90),
- the URA3 gene of *Saccharomyces cerevisiae* coding for orotidine 5'-phosphate decarboxylase (Rose, M., et al., Gene 29 (1984) 113-124) which allows plasmid selection by complementation of *E. coli* ΔpyrF mutant strains (uracil auxotrophy),
- the core-streptavidin expression cassette comprising
    - the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stueber, D., et al. (see before),
    - the core-streptavidin gene,
    - two bacteriophage-derived transcription terminators, the λ-T0 terminator (Schwarz, E., et al., Nature 272 (1978) 410-414) and the fd-terminator (Beck, E. and Zink, B., Gene 1-3 (1981) 35-58),
- the lacI repressor gene from *E. coli* (Farabaugh, P. J., Nature 274 (1978) 765-769).

The final expression plasmid 5836 for the expression of the shortened tetranectin-apolipoprotein A-I fusion protein can be prepared by excising the core-streptavidin structural gene from plasmid 4980 using the singular flanking EcoRI and CelII restriction endonuclease cleavage site and inserting the EcoRI/CelII restriction site flanked nucleic acid encoding the fusion protein into the 3142 bp long EcoRI/CelII-1 plasmid fragment.

d) Plasmid 3036

The expression plasmid 3036 for recombinant production of IgA-Protease is based on the vector OripBR-URA3-EK-IFN (see e.g. U.S. Pat. No. 6,291,245). Plasmid 3036 differs from OripBR-URA3-EK-IFN by the presence of a lad repressor gene and the target gene encoding the IgA protease protein. The lad repressor gene was derived from plasmid pUHA1 (Stueber, D., et al., In: Immunological Methods IV (1990) 121-152). It was amplified by polymerase chain reaction (PCR) according to the method described by Mullis, K. B. and Faloona, F. A. (Methods Enzymology 155 (1987) 335-350), and cloned into plasmid 3036 precursor. The target gene encoding the IgA-protease protein from *Neisseria gonorrhoeae* was generated by PCR and cloned into the expression vector.

The IgA-Protease expression plasmid 3036 comprises the following elements:

- the origin of replication from vector pBR322 for replication in *E. coli* (corresponding to by position 2517-3160 according to Sutcliffe, G., et al., Quant. Biol. 43 (1979) 77-90),
- the URA3 gene of *Saccharomyces cerevisiae* coding for orotidine 5'-phosphate decarboxylase (Rose, M., et al., Gene 29 (1984) 113-124) which allows plasmid selection by complementation of *E. coli* ΔpyrF mutant strains (uracil auxotrophy),
- the IgA-Protease expression cassette comprising
    - the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stueber, D., et al. (see before),
    - Open-reading-frame of IgA Protease (*Neisseria gonorrhoeae*, GenBank Accession No. P09790),
    - two bacteriophage-derived transcription terminators, the λ-T0 terminator (Schwarz, E., et al., Nature 272 (1978) 410-414) and the fd-terminator (Beck, E. and Zink, B., Gene 1-3 (1981) 35-58),
- the lad repressor gene from *E. coli* (Farabaugh, P. J., Nature 274 (1978) 765-769).

Example 3

Expression of a Fusion Polypeptide by Cultivation on a Chemically Defined Minimal Growth Medium that has been Supplemented with the Auxotrophy Complementing Amino Acids Leucine and Proline For the expression of the tetranectin-apolipoprotein A-I fusion protein as reported in WO 2012/028526 an *E. coli* host/vector system which enables an antibiotic-free plasmid selection by complementation of an *E. coli* auxotrophy (pyrF) was employed (see EP 0 972 838 and U.S. Pat. No. 6,291,245).

The *E. coli* K12 strains CSPZ-2 (leuB, proC, trpE, thi-1, ΔpyrF) and CSPZ-6 (thi-1, ΔpyrF) were transformed by electroporation with the expression plasmid 5816 (see Example 2). The transformed *E. coli* cells were first grown at 37° C. on agar plates. A colony picked from this plate was transferred to a 3 mL roller culture and grown at 37° C. to an optical density of 1-2 (measured at 578 nm). Then 1000 µL culture were mixed with 1000 µL sterile 86%-glycerol and immediately frozen at −80° C. for long time storage.

The correct product expression of this clone was first verified in small scale shake flask experiments and analyzed with SDS-Page prior to the transfer to the 10 L fermenter.

Pre-cultivation:

For pre-cultivation a chemical defined medium (CDM) has been used:

NH4Cl 1.0 g/L, K2HPO4*3H2O 18.3 g/L, citrate 1.6 g/L, glycine 0.78 g/L, L-alanine 0.29 g/L, L-arginine 0.41 g/L, L-asparagine*H2O 0.37 g/L, L-aspartate 0.05 g/L, L-cysteine*HCl*H2O 0.05 g/L, L-histidine 0.05 g/L, L-isoleucine 0.31 g/L, L-leucine 0.38 g/L, L-lysine*HCl 0.40 g/L, L-methionine 0.27 g/L, L-phenylalanine 0.43 g/L, L-proline 0.36 g/L, L-serine 0.15 g/L, L-threonine 0.40 g/L, L-tryptophan 0.07 g/L, L-valine 0.33 g/L, L-tyrosine 0.51 g/L, L-glutamine 0.12 g/L, Na-L-glutamate*H2O 0.82 g/L, glucose*H2O 5.0 g/L, trace elements solution 5 mL/L, MgSO4*7H2O 0.86 g/L, thiamin*HCL 17.5 mg/L.

The trace elements solution contains MnSO4*H2O 1.28 g/l, ZnSO4*7H2O 1.70 g/L, H3BO3 0.30 g/L, (NH4)6Mo7O24*4H2O 0.18 g/L, CoCl2*6H2O 0.25 g/L, CuSO4*5H2O 0.22 g/L, EDTA 0.75 g/L.

For pre-cultivation 300 mL of the CDM in a 1000 mL Erlenmeyer-flask with four baffles was inoculated with 0.9 mL out of a primary seed bank ampoule. The cultivation was performed on a rotary shaker for 9 hours at 37° C. and 170 rpm until an optical density (578 nm) of 7-13 was obtained. 100 g of this pre-cultivation was then transferred to the 10 L bioreactor to inoculate the batch medium.

Fermentation with Amino Acids L-Leucine and L-Proline (Experiment No. 1 and Experiment No. 2):

For fermentation in a 10 L Biostat C, DCU3 fermenter (Sartorius, Melsungen, Germany) the following batch medium was used: KH2PO4 4.73 g/L, (NH4)2HPO4 7.47 g/L, K2HPO4*3H2O 14.94 g/L, citrate 2.07 g/L, L-methionine 1.22 g/L, L-proline 4.08 g/L, L-leucine 2.57 g/L, ammonium ferric citrate 0.08 g/L, NaHCO3 0.82 g/L, trace elements solution 7.3 mL/L, MgSO4*7H2O 1.42 g/L, thiamine*HCl 20.9 mg/L, glucose*H2O 29.3 g/L, biotin 0.2 mg/L, 1.2 mL/L Synperonic 10% anti foam agent.

The trace elements solution contains FeSO4*7H2O 10 g/L, ZnSO4*7H2O 2.25 g/L, MnSO4*H2O 2.13 g/L, CuSO4*5H2O 1.0 g/L, CoCl2*6H2O 0.42 g/L, (NH4)6Mo7O24*4H2O 0.3 g/L, H3BO3 0.50 g/L, thiamine-HCL 2.0 g/L solubilized in 1N HCl solution.

The feed 1 solution contained 700 g/L glucose*H2O, KH2PO4 8.43 g/L and K2HPO4*3H2O 22.38 g/L.

Feed 2 comprises 585 g/L L-proline and 150.3 g/L MgSO4*7H2O.

All components were dissolved in deionized water.

The alkaline solution for pH regulation was an aqueous 12.5% (w/v) NH3 solution supplemented with 11.25 g/L L-methionine, 51.5 g/L L-proline and 56.25 g/L L-leucine (see WO 2012/028522).

Starting with 4.2 L sterile batch medium plus 100 mL inoculum from the pre-cultivation the batch fermentation was performed at 37° C., pH 6.9±0.2, 800 mbar back pressure and an initial aeration rate of 10 L/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 25° C. and 15 minutes later the fermentation entered the fed-batch mode with the start of both feeds (50 and 13 g/h respectively). The rate of feed 2 is kept constant, while the rate of feed 1 is increased stepwise with a predefined feeding profile from 50 to finally 160 g/h within 8.5 hours. When carbon dioxide off gas concentration leveled above 2% the aeration rate was constantly increased from 10 to 20 L/min within 5 hours. The expression of recombinant tetranectin-apolipoprotein A-1 fusion protein was induced by the addition of 2.4 g IPTG at an optical density of 150.

At the end of fermentation the within the cytoplasm soluble expressed tetranectin-apolipoprotein A-1 fusion protein was transferred to insoluble protein aggregates, the so called inclusion bodies, with a heat step where the whole culture broth in the fermenter is heated to 50° C. for 1 hour before harvest (see e.g. EP-B 1 486 571). Thereafter, the content of the fermenter was centrifuged with a flow-through centrifuge (13,000 rpm, 13 L/h) and the harvested biomass was stored at −20° C. until further processing. The synthesized tetranectin-apolipoprotein A-1 fusion proteins were found exclusively in the insoluble cell debris fraction in the form of insoluble protein aggregates, so-called inclusion bodies (IBs).

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OE_{target}=5$) are suspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 µL and to each pellet (=insoluble) fraction 400 µL of SDS sample buffer (Laemmli, U. K., Nature 227 (1970) 680-685) are added. Samples are heated for 15 minutes at 95° C. under intense mixing to solubilize and reduce all proteins in the samples. After cooling to room temperature 5 µL of each sample are transferred to a 4-20% TGX Criterion Stain Free polyacrylamide gel (Bio-Rad). Additionally 5 µL molecular weight standard (Precision Plus Protein Standard, Bio-Rad) and 3 amounts (0.3 µL, 0.6 µL and 0.9 µL) quantification standard with known product protein concentration (0.1 µg/4) are positioned on the gel.

The electrophoresis was run for 60 min. at 200 V and thereafter the gel was transferred to a GelDOC EZ Imager (Bio-Rad) and processed for 5 min. with UV radiation. Gel images were analyzed using Image Lab analysis software (Bio-Rad). With the three standards a linear regression curve was calculated with a coefficient of >0.99 and thereof the concentrations of target protein in the original sample was calculated.

The activity of the purified and lipidated TN-ApoA1 was measured in an eight day radioactive efflux assay. Cells (THP-1) were differentiated by PMA (phorbol myristate acetate) to macrophages. These cells were loaded with acetylated LDL and $^3H$-labeled cholesterol. The supernatant was discarded and cells were incubated for 5 hours with equilibration medium to remove non-specifically bound cholesterol. The lipidated TN-ApoA1 was added which enabled the export of the $^3H$-labeled cholesterol out of the cells during the following 18 hours. Radioactivity was measured in the supernatant and in the cell lysate.

Results:

The above mentioned fermentation process was used to express tetranectin-apolipoprotein A-1 in the parental strain CSPZ-2 which is auxotrophic against L-leucine and L-proline and in the auxotrophy cured strain CSPZ-6. Despite the latter strain does not need the feeding of the amino acids L-leucine and L-proline any more, the performance of this auxotrophy cured strain was tested with the supplemented fermentation medium for direct performance comparison to strain CSPZ-2.

The auxotrophy cured strain is growing faster than the parental strain despite the same medium and fermentation process was used (see FIG. 1).

Figure 2:
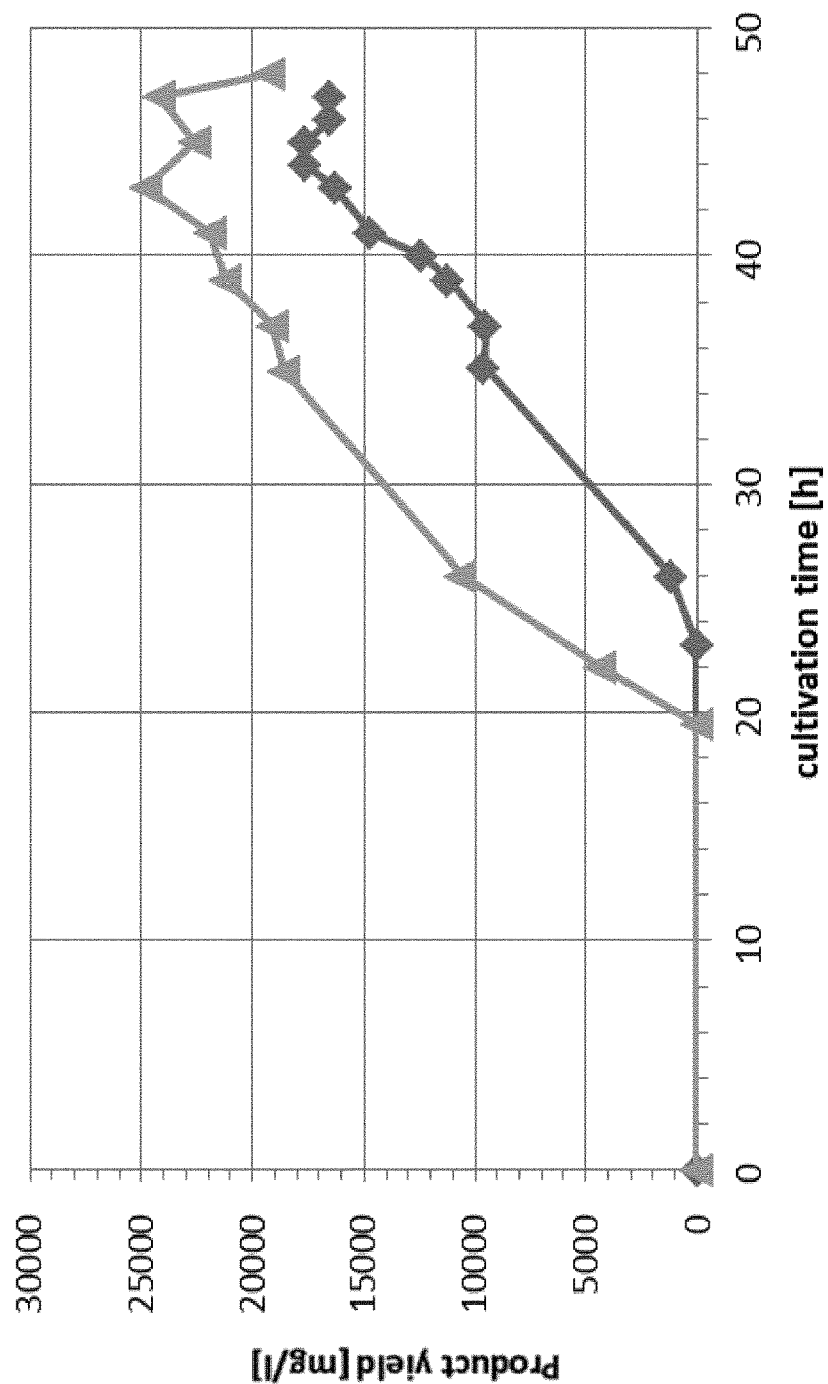
FIG. 2 Product yield comparison of parental strain CSPZ-2 (diamonds) and auxotrophy cured strain CSPZ-6 (triangles).

The auxotrophy cured strain is faster expressing more product than the parental strain despite the same medium and fermentation process was used (see FIG. 2).

As can be seen from the concentration trends of the amino acids leucine and proline (see FIGS. 3 A and B) the auxotrophy cured strain can now metabolize L-leucine and L-proline due to intact metabolic pathways. Therefore the growth of the auxotrophy cured strain is faster under glucose limited cultivation conditions of the applied fed-batch process.

Surprisingly the auxotrophy cured strain had a significant better performance than the parental strain on the same chemical defined fermentation medium supplemented with the amino acids L-leucine and L-proline. The growth is accelerated due to the possibility to metabolize the contained amino acids and this may also improve product formation. The conclusion from this is to use a prototroph E. coli production strain.

Example 4

Expression of IgA Protease by Cultivation on a Chemically Defined Minimal Growth Medium that has been Supplemented with the Auxotrophy Complementing Amino Acids Leucine and Proline For the expression of IgA-Protease (106 kDa) the E. coli host/vector system which enables an antibiotic-free plasmid selection by complementation of an E. coli auxotrophy (PyrF) was employed (see EP 0 972 838 and U.S. Pat. No. 6,291,245).

The E. coli K12 strains CSPZ-2 (leuB, proC, trpE, thi-1, ΔpyrF) and CSPZ-6 (thi-1, ΔpyrF) were transformed by electroporation with the expression plasmid 3036. The transformed E. coli cells were first grown at 37° C. on agar plates. A colony picked from this plate was transferred to a 3 mL roller culture and grown at 37° C. to an optical density of 1-2 (measured at 578 nm). Then 1000 μL culture were mixed with 1000 μL sterile 86%-glycerol and immediately frozen at −80° C. for long time storage. The correct product expression of this clone was first verified in small scale shake flask experiments and analyzed with SDS-Page prior to the transfer to the 10 L fermenter.

Pre-cultivation:

For pre-cultivation a chemical defined medium (CDM) has been used:

NH4Cl 1.0 g/L, K2HPO4*3H2O 18.3 g/L, citrate 1.6 g/L, glycine 0.78 g/L, L-alanine 0.29 g/L, L-arginine 0.41 g/L, L-asparagine*H2O 0.37 g/L, L-aspartate 0.05 g/L, L-cysteine*HCl*H2O 0.05 g/L, L-histidine 0.05 g/L, L-isoleucine 0.31 g/L, L-leucine 0.38 g/L, L-lysine*HCl 0.40 g/L, L-methionine 0.27 g/L, L-phenylalanine 0.43 g/L, L-proline 0.36 g/L, L-serine 0.15 g/L, L-threonine 0.40 g/L, L-tryptophan 0.07 g/L, L-valine 0.33 g/L, L-tyrosine 0.51 g/L, L-glutamine 0.12 g/L, Na-L-glutamate*H2O 0.82 g/L, glucose*H2O 6.0 g/L, trace elements solution 0.5 mL/L, MgSO4*7H2O 0.86 g/L, thiamin*HCl 17.5 mg/L.

The trace elements solution contains FeSO4*7H2O 10.0 g/L, ZnSO4*7H2O 2.25 g/L, MnSO4*H2O 2.13 g/L, H3BO3 0.50 g/L, (NH4)6Mo7O24*4H2O 0.3 g/L, CoCl2*6H2O 0.42 g/L, CuSO4*5H2O 1.0 g/L dissolved in 0.5M HCl.

For pre-cultivation 220 ml of CDM in a 1000 mL Erlenmeyer-flask with four baffles was inoculated with 1.0 mL out of a primary seed bank ampoule. The cultivation was performed on a rotary shaker for 9 hours at 37° C. and 170 rpm until an optical density (578 nm) of 11-13 was obtained. The inoculum volume was calculated with $V_{inoc.}=100$ mL*5/$OD_{PC}$ and is dependent on the optical density of the pre-cultivation to inoculate the batch medium of the 10 L bioreactor with equal amount of cells.

Fermentation with Amino Acids L-Leucine and L-Proline (Experiment No. 3 and Experiment No. 4):

For fermentation in a 10 L Biostat C, DCU3 fermenter (Sartorius, Melsungen, Germany) the same process as described in Example 3 was performed except that no heat step was conducted at the end of the fermentations.

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OE_{target}$=10) are suspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 100 μL and to each pellet (=insoluble) fraction 200 μL of SDS sample buffer (Laemmli, U. K., Nature 227 (1970) 680-685) are added. Samples are heated for 15 min. at 95° C. under intense mixing to solubilize and reduce all proteins in the samples. After cooling to room temperature 5 μL of each sample are transferred to a 4-20% TGX Criterion Stain Free polyacrylamide gel (Bio-Rad). Additionally 5 μL molecular weight standard (Precision Plus Protein Standard, Bio-Rad) and 3 amounts (0.3 μL, 0.6 μL and 0.9 μL) quantification standard with known product protein concentration (0.1 μg/μL) are positioned on the gel.

The electrophoresis was run for 60 min. at 200 V and thereafter the gel was transferred the GelDOC EZ Imager (Bio-Rad) and processed for 5 min. with UV radiation. Gel images were analyzed using Image Lab analysis software (Bio-Rad). With the three standards a linear regression curve was calculated with a coefficient of >0.99 and thereof the concentrations of target protein in the original sample was calculated.

Results:

The above mentioned fermentation process was used to express IgA protease in the parental strain CSPZ-2 which is auxotrophic against L-Leucine and L-Proline and in the auxotrophy cured strain CSPZ-6. Despite the latter strain does not need the feeding of the amino acids L-Leucine and L-Proline any more, the performance of this auxotrophy cured strain on the supplemented fermentation medium for direct performance comparison to parental strain CSPZ-2 has been tested.

The growth of the auxotrophy cured strain on amino acid supplemented batch medium was significant faster compared to the parental strain.

Example 5

Cultivation of an Auxotrophy Cured E. coli Strain and the Wild-type Strain MG1655 on a Chemically Defined Minimal Growth Medium One clear benefit of an auxotrophy cured strain is that no more expensive amino acids are needed to be fed during cultivation on chemical defined medium due to the prototrophic phenotype. This would dramatically reduce costs of goods for the process. To test an identical fermentation with the auxotrophy cured strain CSPZ-6 was conducted where simply the amino acids L-leucine and L-proline were excluded from the medium and feeds. To demonstrate that the auxotrophy cured strain has significant advantages over a wild-type E. coli strain which is also prototrophic growth and product formation of the K12 strain MG1655 (with deleted pyrF gene to fit to the antibiotic free selection system) within the same fermentation process was explored.

The *E. coli* K12 strains CSPZ-6 (thi-1, ΔpyrF) and MG1655 derivative (ΔpyrF, ΔompT) were transformed by electroporation with the expression plasmid 5816 (see Example 2). The transformed *E. coli* cells were first grown at 37° C. on agar plates. A colony picked from this plate was transferred to a 3 mL roller culture and grown at 37° C. to an optical density of 1-2 (measured at 578 nm). Then 1000 µL culture were mixed with 1000 µL sterile 86%-glycerol and immediately frozen at −80° C. for long time storage.

The correct product expression of this clone was first verified in small scale shake flask experiments and analyzed with SDS-Page prior to the transfer to the 10 L fermenter.
Pre-cultivation:

For pre-cultivation a chemical defined medium (CDM) has been used:

$NH_4Cl$ 1.0 g/L, $K_2HPO_4*3H_2O$ 18.3 g/L, citrate 1.6 g/L, glycine 0.78 g/L, L-alanine 0.29 g/L, L-arginine 0.41 g/L, L-asparagine*$H_2O$ 0.37 g/L, L-aspartate 0.05 g/L, L-cysteine*HCl*$H_2O$ 0.05 g/L, L-histidine 0.05 g/L, L-isoleucine 0.31 g/L, L-leucine 0.38 g/L, L-lysine*HCl 0.40 g/L, L-methionine 0.27 g/L, L-phenylalanine 0.43 g/L, L-proline 0.36 g/L, L-serine 0.15 g/L, L-threonine 0.40 g/L, L-tryptophan 0.07 g/L, L-valine 0.33 g/L, L-tyrosine 0.51 g/L, L-glutamine 0.12 g/L, Na-L-glutamate*$H_2O$ 0.82 g/L, glucose*$H_2O$ 5.0 g/L, trace elements solution 5 mL/L, $MgSO_4*7H_2O$ 0.86 g/L, thiamin*HCl 17.5 mg/L.

The trace elements solution contains $MnSO_4*H_2O$ 1.28 g/L, $ZnSO_4*7H_2O$ 1.70 g/L, $H_3BO_3$ 0.30 g/L, $(NH_4)_6Mo_7O_{24}*4H_2O$ 0.18 g/L, $CoCl_2*6H_2O$ 0.25 g/L, $CuSO_4*5H_2O$ 0.22 g/L, EDTA 0.75 g/L.

For pre-cultivation 300 mL of CDM medium in a 1000 mL Erlenmeyer-flask with four baffles was inoculated with 0.9 mL out of a primary seed bank ampoule. The cultivation was performed on a rotary shaker for 9 hours at 37° C. and 170 rpm until an optical density (578 nm) of 6-13 was obtained. 100 g of this pre-cultivation was then transferred to the 10 L bioreactor to inoculate the batch medium.
Fermentation without Amino Acids L-Leucine and L-Proline (Experiment No. 5 and Experiment No. 6):

For fermentation in a 10 L Biostat C, DCU3 fermenter (Sartorius, Melsungen, Germany) the following batch medium was used: $KH_2PO_4$ 4.73 g/L, $(NH_4)_2HPO_4$ 7.47 g/L, $K_2HPO_4*3H_2O$ 14.94 g/L, citrate 2.07 g/L, L-methionine 1.22 g/L, ammonium ferric citrate 0.08 g/L, $NaHCO_3$ 0.82 g/L, trace elements solution 7.3 mL/L, $MgSO_4*7H_2O$ 1.42 g/L, thiamine*HCl 20.9 mg/L, glucose*$H_2O$ 29.3 g/L, biotin 0.2 mg/L, 1.2 mL/L Synperonic 10% anti foam agent.

The trace elements solution contains $FeSO_4*7H_2O$ 10 g/L, $ZnSO_4*7H_2O$ 2.25 g/L, $MnSO_4*H_2O$ 2.13 g/L, $CuSO_4*5H_2O$ 1.0 g/L, $CoCl_2*6H_2O$ 0.42 g/L, $(NH_4)_6Mo_7O_{24}*4H_2O$ 0.3 g/L, $H_3BO_3$ 0.50 g/L, thiamine-HCl 2.0 g/L solubilized in 1N HCl solution.

The feed 1 solution contained 700 g/L glucose*$H_2O$, $KH_2PO_4$ 8.43 g/L and $K_2HPO_4*3H_2O$ 22.38 g/L.

Feed 2 comprises only 150.3 g/L $MgSO_4*7H_2O$.

All components were dissolved in deionized water.

The alkaline solution for pH regulation was an aqueous 12.5% (w/v) $NH_3$ solution supplemented with 11.25 g/L L-methionine.

Starting with 4.2 L sterile batch medium plus 100 mL inoculum from the pre-cultivation the batch fermentation was performed at 37° C., pH 6.9±0.2, 800 mbar back pressure and an initial aeration rate of 10 L/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 25° C. and 15 minutes later the fermentation entered the fed-batch mode with the start of both feeds (50 and 13 g/h respectively). The rate of feed 2 is kept constant, while the rate of feed 1 is increased stepwise with a predefined feeding profile from 50 to finally 160 g/h within 8.5 hours. When carbon dioxide off gas concentration leveled above 2% the aeration rate was constantly increased from 10 to 20 L/min within 5 hours. The expression of recombinant tetranectin-apolipoprotein A-1 fusion protein was induced by the addition of 2.4 g IPTG at an optical density of 150. At the end of fermentation the within the cytoplasm soluble expressed tetranectin-apolipoprotein A-I is transferred to insoluble protein aggregates, the so called inclusion bodies, with a heat step where the whole culture broth in the fermenter is heated to 50° C. for one hour before harvest (see e.g. EP-B 1 486 571). Thereafter, the content of the fermenter was centrifuged with a flow-through centrifuge (13,000 rpm, 13 l/h) and the harvested biomass was stored at −20° C. until further processing. The synthesized tetranectin-apolipoprotein A-I fusion proteins were found exclusively in the insoluble cell debris fraction in the form of insoluble protein aggregates, so-called inclusion bodies (IBs).
Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OE_{target}$=5) are suspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 µL and to each pellet (=insoluble) fraction 400 µL of SDS sample buffer (Laemmli, U. K., Nature 227 (1970) 680-685) are added. Samples are heated for 15 minutes at 95° C. under intense mixing to solubilize and reduce all proteins in the samples. After cooling to room temperature 5 µL of each sample are transferred to a 4-20% TGX Criterion Stain Free polyacrylamide gel (Bio-Rad). Additionally 5 µL molecular weight standard (Precision Plus Protein Standard, Bio-Rad) and 3 amounts (0.3 µL, 0.6 µL and 0.9 µL) quantification standard with known product protein concentration (0.1 µg/µL) are positioned on the gel.

The electrophoresis was run for 60 min. at 200 V and thereafter the gel was transferred the GelDOC EZ Imager (Bio-Rad) and processed for 5 min. with UV radiation. Gel images were analyzed using Image Lab analysis software (Bio-Rad). With the three standards a linear regression curve was calculated with a coefficient of >0.99 and thereof the concentrations of target protein in the original sample was calculated.

The activity of the purified and lipidated TN-ApoA1 was measured in an eight day radioactive efflux assay. Cells (THP-1) were differentiated by PMA (phorbol myristate acetate) to macrophages. These cells were loaded with acetylated LDL and $^3H$-labeled cholesterol. The supernatant was discarded and cells were incubated for 5 hours with equilibration medium to remove non-specifically bound cholesterol. The lipidated TN-ApoA1 was added which enabled the export of the $^3H$-labeled cholesterol out of the cells during the following 18 hours. Radioactivity was measured in the supernatant and in the cell lysate.
Results:

The above mentioned fermentation process was used to express tetranectin-apolipoprotein A-I in the auxotrophy cured strain CSPZ-6 and the prototrophic MG1655 derivative strain representing the K12 wild-type strain MG1655. Both strains do not need the feeding of the amino acids L-leucine and L-proline which where consequently excluded from the medium and feeds. This distinctly reduces cost of goods for the process.

Figure 4:
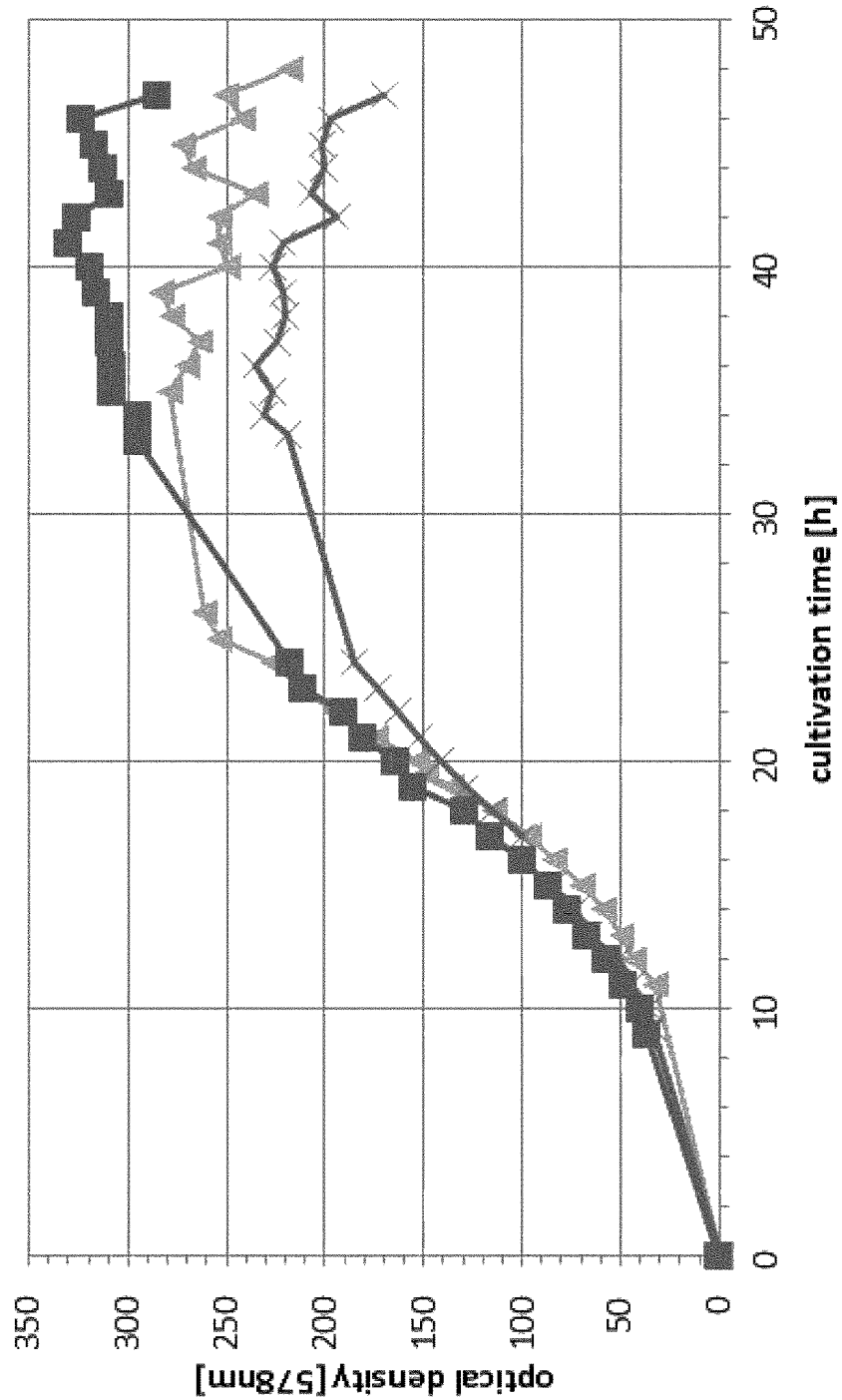
FIG. 4 Growth comparison of auxotrophy cured and wild-type strain on medium with and without amino acid supplementation (CSPZ-6 on CDM supplemented with L-leucine and L-proline: triangle; CSPZ-6 on CDM: squares; MG1655 derivative strain on CDM: "X")
FIG. 5 Product yield comparison of auxotrophy cured and wild-type strain on medium with and without amino acid supplementation (CSPZ-6 on CDM supplemented with L-leucine and L-proline: triangle; CSPZ-6 on CDM: squares; MG1655 derivative strain on CDM: "X").

Both, the auxotrophy cured and the wild-type strain are growing faster on medium without the amino acids L-leucine and L-proline due to the lack of growth inhibitory effects of higher concentrations of L-leucine (see Example 3). Final optical density of the auxotrophy cured strain is well improved in this medium lacking the amino acids, while the growth of the wild-type strain is significant reduced after induction of product formation and in the late phase of fermentation (see FIG. 4).

Figure 5:
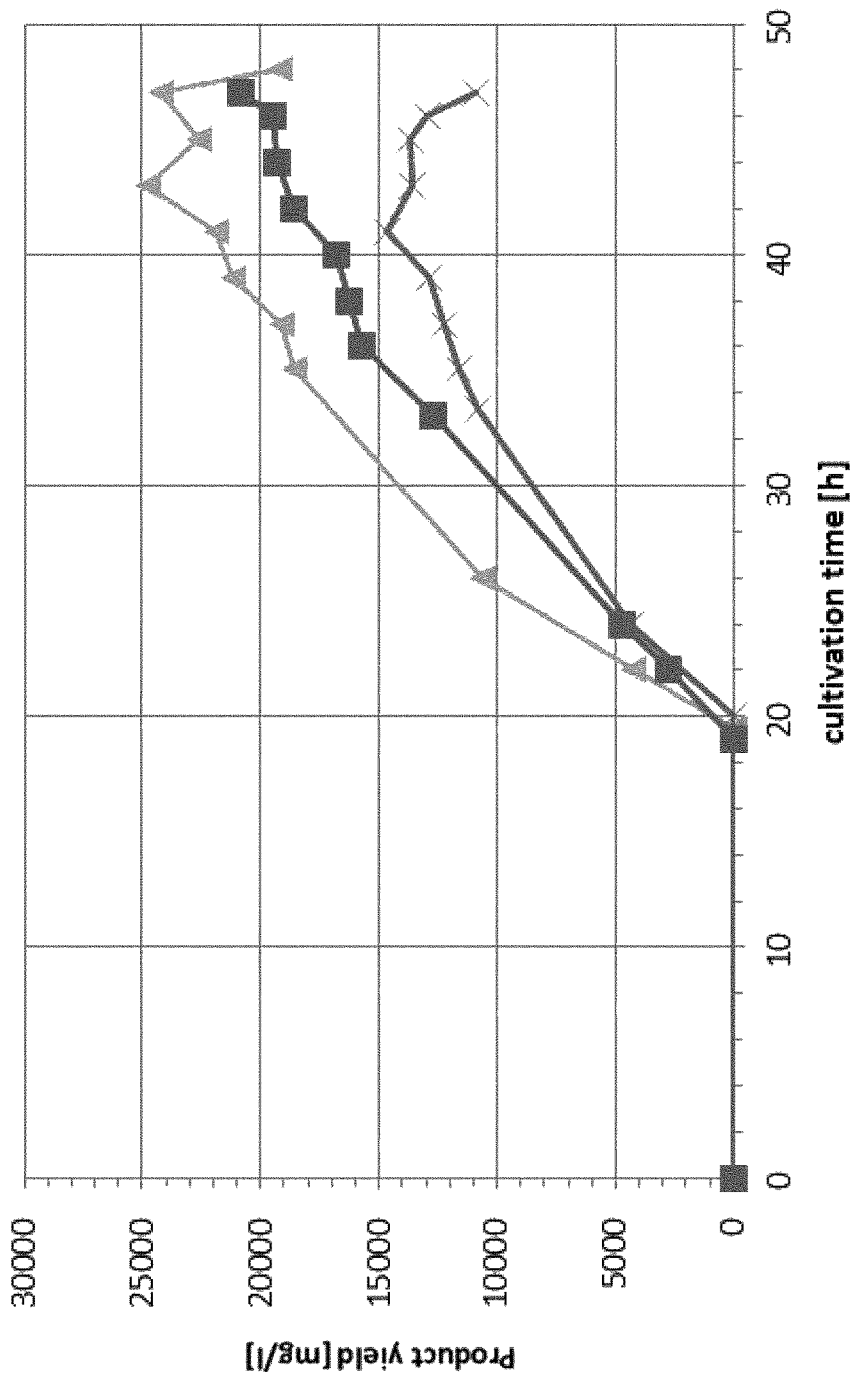

Despite the product formation of the auxotrophy cured strain in the first few hours after inductor addition is faster in the fermentation medium supplemented with amino acids the final yield is nearly the same compared to the fermentation without amino acids addition (see FIG. 5). Therefore the leave of the amino acids from the medium saves significant costs but does not reduce product yields. The prototroph wild-type E. coli MG1655 derivative strain has significant deficiencies in yields of growth and product.

Summary:

The auxotrophy cured strain showed a better performance than a prototroph wild-type E. coli strain on the same chemical defined fermentation medium even if the amino acids L-leucine and L-proline are not supplemented. Therefore it is advantageous to cure high producing E. coli strains from their amino acid auxotrophies in order to allow a cultivation on chemically defined minimal growth medium and profit from the advantages of using such a chemically defined minimal growth medium instead of using a prototrophic wild-type E. coli strain like MG1655 or the closely related W3110 (Vijayendran, C., et al., J. Biotechnol. 128 (2007) 747-761) as can further be seen in Example 6.

Example 6

Cultivation of an Auxotrophy Cured E. coli Strain and the Wild-type Strain W3110 on a Chemically Defined Minimal Growth Medium To demonstrate that the auxotrophy cured strain CSPZ-6 has significant advantages over the prototrophic wild-type E. coli strain W3110 (with deleted pyrF gene to fit to the antibiotic free selection system) growth and product formation within the same fermentation process was explored.

The E. coli K12 strains CSPZ-6 (thi-1, ΔpyrF) and 66C5 (=W3110 ΔpyrF derivate) were transformed by electroporation with the expression plasmid 5830 (see Example 2). The transformed E. coli cells were first grown at 37° C. on agar plates. A colony picked from this plate was transferred to a 3 mL roller culture and grown at 37° C. to an optical density of 1-2 (measured at 578 nm). Then 1000 µL culture were mixed with 1000 mL sterile 86%-glycerol and immediately frozen at −80° C. for long time storage.

The correct product expression of this clone was first verified in small scale shake flask experiments and analyzed with SDS-Page prior to the transfer to the 10 L fermenter.

Pre-cultivation:

For pre-cultivation a chemical defined medium (CDM) has been used:

NH4Cl 1.0 g/L, K2HPO4*3H2O 18.3 g/L, citrate 1.6 g/L, glycine 0.78 g/L, L-alanine 0.29 g/L, L-arginine 0.41 g/L, L-asparagine*H2O 0.37 g/L, L-aspartate 0.05 g/L, L-cysteine*HCl*H2O 0.05 g/L, L-histidine 0.05 g/L, L-isoleucine 0.31 g/L, L-leucine 0.38 g/L, L-lysine*HCl 0.40 g/L, L-methionine 0.27 g/L, L-phenylalanine 0.43 g/L, L-proline 0.36 g/L, L-serine 0.15 g/L, L-threonine 0.40 g/L, L-tryptophan 0.07 g/L, L-valine 0.33 g/L, L-tyrosine 0.51 g/L, L-glutamine 0.12 g/L, Na-L-glutamate*H2O 0.82 g/L, glucose*H2O 5.0 g/L, trace elements solution 5 mL/L, MgSO4*7H2O 0.86 g/L, thiamin*HCl 17.5 mg/L.

The trace elements solution contains FeSO4*7H2O 10.0 g/L, ZnSO4*7H2O 2.25 g/L, MnSO4*H2O 2.13 g/L, H3BO3 0.50 g/L, (NH4)6Mo7O24*4H2O 0.3 g/L, CoCl2*6H2O 0.42 g/L, CuSO4*5H2O 1.0 g/L dissolved in 0.5 M HCl.

For pre-fermentation 300 ml of CDM-medium in a 1000 ml Erlenmeyer-flask with four baffles was inoculated with 0.9 ml out of a primary seed bank ampoule. The cultivation was performed on a rotary shaker for 8 hours at 32° C. and 170 rpm until an optical density (578 nm) of 4-9 was obtained. The inoculum volume was calculated with $V_{inoc.}$=100 ml*5/ODPC and is dependent on the optical density of the pre cultivation to inoculate the batch medium of the 10 L bioreactor with equal amount of cells.

Fermentation without Amino Acids L-Leucine and L-Proline (Experiment No. 7 and Experiment No. 8):

For fermentation in a 10 L Biostat C, DCU3 fermenter (Sartorius, Melsungen, Germany) the following batch medium was used: KH2PO4 1.58 g/L, (NH4)2HPO4 7.47 g/L, K2HPO4*3H2O 13.32 g/L, citrate 2.07 g/L, L-methionine 1.22 g/L, NaHCO3 0.82 g/L, trace elements solution 7.3 mL/L, MgSO4*7H2O 0.99 g/L, thiamine*HCl 20.9 mg/L, glucose*H2O 29.3 g/L, biotin 0.2 mg/L, 1.2 mL/L Synperonic 10% anti foam agent.

The trace elements solution contains FeSO4*7H2O 10 g/L, ZnSO4*7H2O 2.25 g/L, MnSO4*H2O 2.13 g/L, CuSO4*5H2O 1.0 g/L, CoCl2*6H2O 0.42 g/L, (NH4)6Mo7O24*4H2O 0.3 g/L, H3BO3 0.50 g/L solubilized in 0.5M HCl solution.

The feed 1 solution contained 700 g/L glucose*H2O, 12.3 g/L MgSO4*7H2O and 0.1 g/L FeSO4*7H2O.

Feed 2 comprises KH2PO4 52.7 g/L, K2HPO4*3H2O 139.9 g/L and (NH4)2HPO4 132.1 g/L.

All components were dissolved in deionized water.

The alkaline solution for pH regulation was an aqueous 12.5% (w/v) NH3 solution supplemented with 11.25 g/L L-methionine.

Starting with 4.2 L sterile batch medium plus 100 mL inoculum from the pre cultivation the batch fermentation was performed at 31° C., pH 6.9±0.2, 800 mbar back pressure and an initial aeration rate of 10 L/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 25° C. and 15 minutes later the fermentation entered the fed-batch mode with the start of both feeds (60 and 14 g/h respectively). The rate of feed 2 is kept constant, while the rate of feed 1 is increased stepwise with a predefined feeding profile from 60 to finally 160 g/h within 7 hours. When carbon dioxide off gas concentration leveled above 2% the aeration rate was constantly increased from 10 to 20 L/min within 5 hours. The expression of recombinant tetranectin-apolipoprotein A-I fusion protein was induced by the addition of 2.4 g IPTG at an optical density of 120. At the end of fermentation the within the cytoplasm soluble expressed tetranectin-apolipoprotein A-I is transferred to insoluble protein aggregates, the so called inclusion bodies, with a heat step where the whole culture broth in the fermenter is heated to 50° C. for 1 hour before harvest (see e.g. EP-B 1 486 571). Thereafter, the content of the fermenter was centrifuged with a flow-through centrifuge (13,000 rpm, 13 L/h) and the harvested biomass was stored at −20° C. until further processing. The synthesized tetranectin-apolipoprotein A-I fusion proteins were found exclusively in the insoluble cell debris fraction in the form of insoluble protein aggregates, so-called inclusion bodies (IBs).

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OE_{target}$=5) are suspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 μL and to each pellet (=insoluble) fraction 400 μL of SDS sample buffer (Laemmli, U. K., Nature 227 (1970) 680-685) are added. Samples are heated for 15 minutes at 95° C. under intense mixing to solubilize and reduce all proteins in the samples. After cooling to room temperature 5 μL of each sample are transferred to a 4-20% TGX Criterion Stain Free polyacrylamide gel (Bio-Rad). Additionally 5 μL molecular weight standard (Precision Plus Protein Standard, Bio-Rad) and 3 amounts (0.3 μL, 0.6 μL and 0.9 μL) quantification standard with known product protein concentration (0.1 μg/μL) are positioned on the gel.

The electrophoresis was run for 60 min. at 200 V and thereafter the gel was transferred the GelDOC EZ Imager (Bio-Rad) and processed for 5 min. with UV radiation. Gel images were analyzed using Image Lab analysis software (Bio-Rad). With the three standards a linear regression curve was calculated with a coefficient of >0.99 and thereof the concentrations of target protein in the original sample was calculated.

The activity of the purified and lipidated TN-ApoA1 was measured in an eight day radioactive efflux assay. Cells (THP-1) were differentiated by PMA (phorbol myristate acetate) to macrophages. These cells were loaded with acetylated LDL and $^3$H-labeled cholesterol. The supernatant was discarded and cells were incubated for 5 hours with equilibration medium to remove non-specifically bound cholesterol. The lipidated TN-ApoA1 was added which enabled the export of the $^3$H-labeled cholesterol out of the cells during the following 18 hours. Radioactivity was measured in the supernatant and in the cell lysate.

Figure 6:
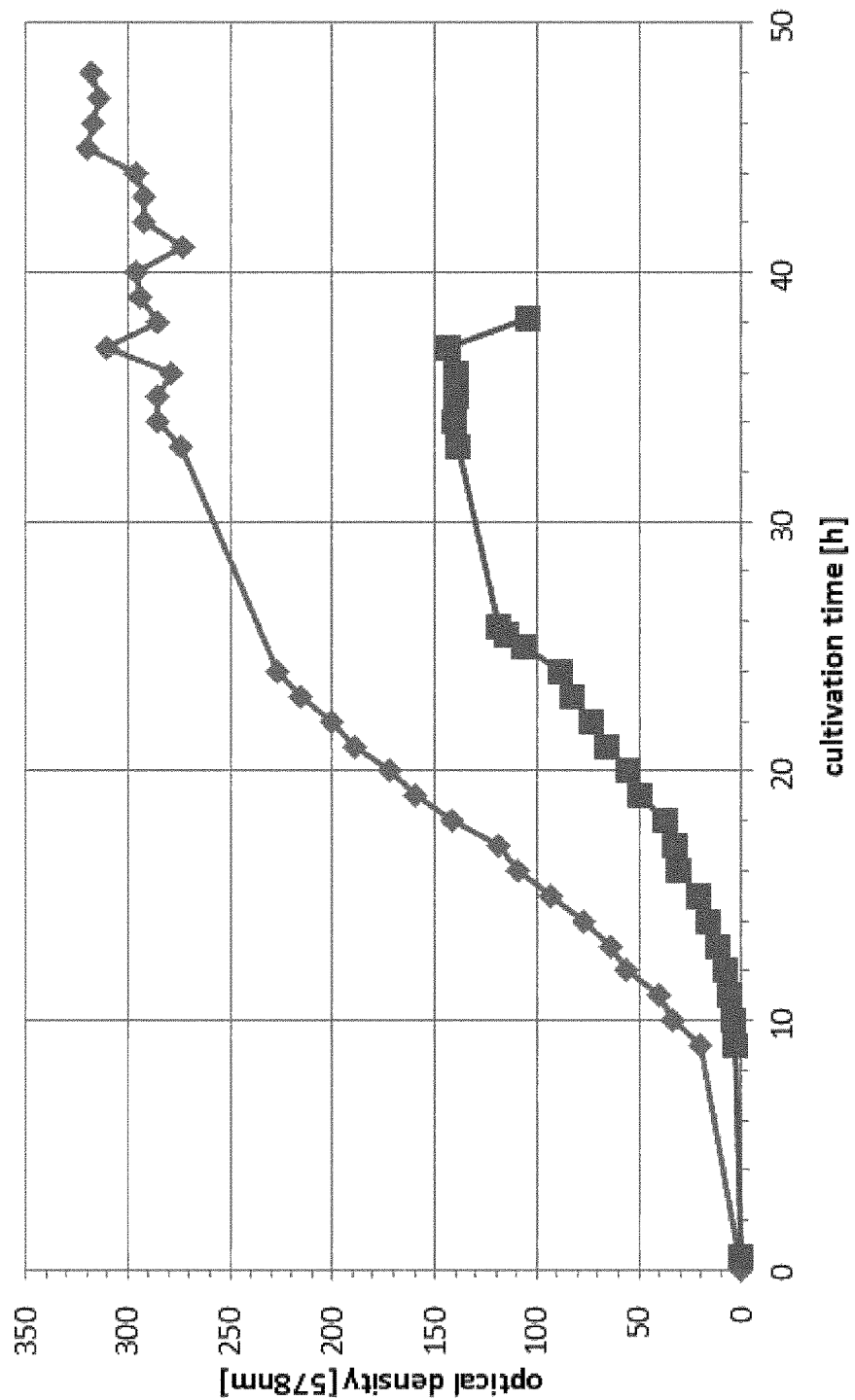
FIG. 6 Growth comparison of auxotrophy cured strain CSPZ-6 (diamonds) and wild-type strain 66C5 (squares) on medium without amino acid supplementation.
Figure 7:
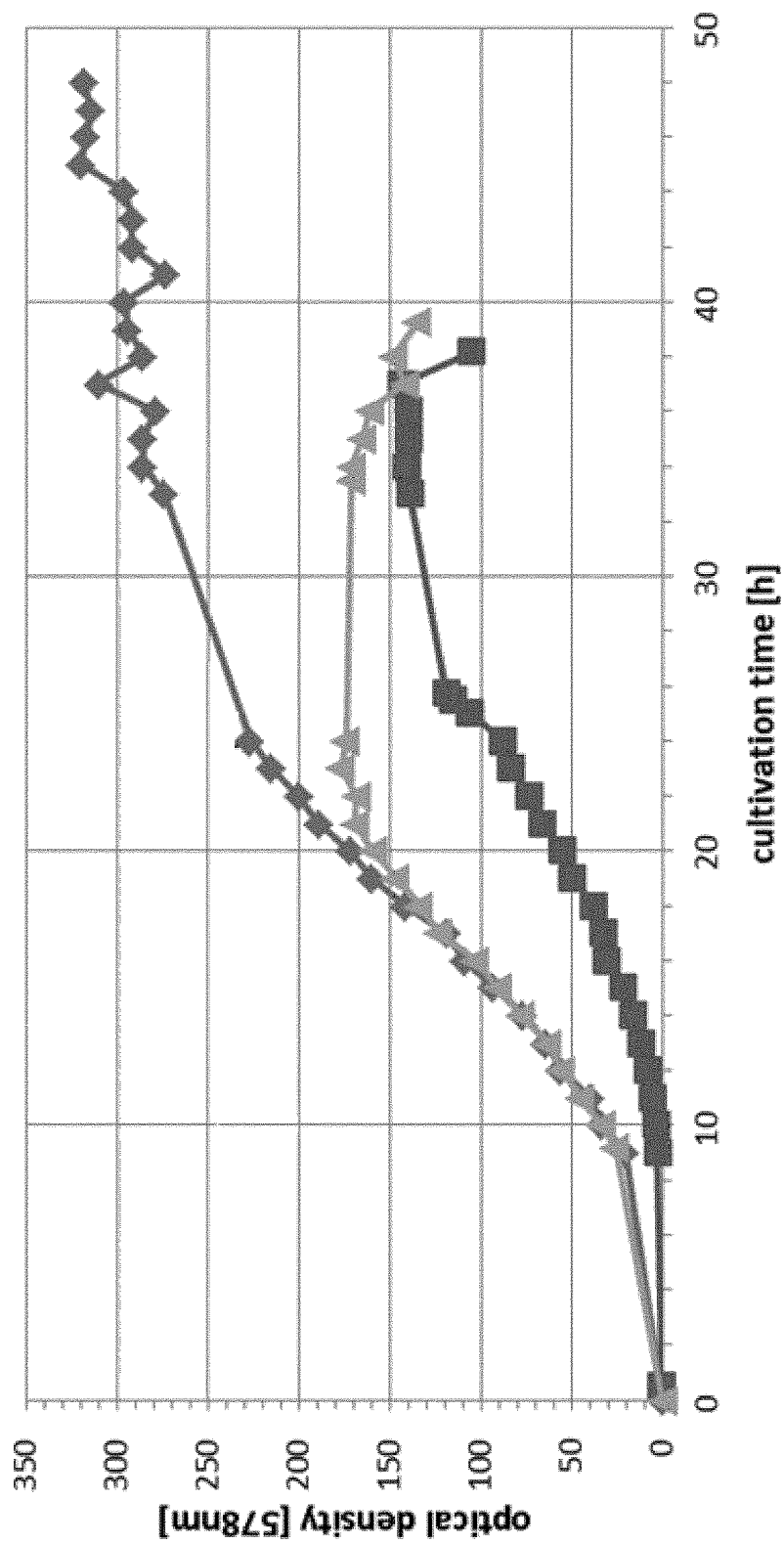
FIG. 7 Growth comparison of auxotrophy cured strain CSPZ-6 (diamonds, normal temperature), wild-type strain 66C5 (squares, normal temperature), and wild-type strain 66C5 at elevated temperature (triangles) on medium without amino acid supplementation.

Results:

The above mentioned fermentation process was used to express tetranectin-apolipoprotein A-I in the auxotrophy cured strain CSPZ-6 and the prototrophic strain 66C5 representing the K12 wild-type strain W3110. Both strains do not need the feeding of the amino acids L-leucine and L-proline which where consequently excluded from the medium and feeds. This reduces cost of goods for the process. Surprisingly the wild-type strain 66C5 despite being prototrophic and inoculated with the equal amount of cells grew extremely slow from the start when compared to the auxotrophy cured strain CSPZ-6 on the same chemically defined medium and under the same cultivation conditions (see FIG. 6). As a consequence the glucose feed rates had to be adapted to avoid overfeeding and glucose accumulation in the medium. Also the final optical densities differ greatly between both strains. While the auxotrophy cured strain reached more than 300 the wild-type strain only obtained 143 and fermentation was terminated due to growth stagnation. The fermentation with the strain 66C5 was repeated with elevated temperatures (experiment no. 9) for batch phase (37° C.) and fed-batch phase (30° C.), but growth yield could not be improved very much (see FIG. 7).

Figure 8:
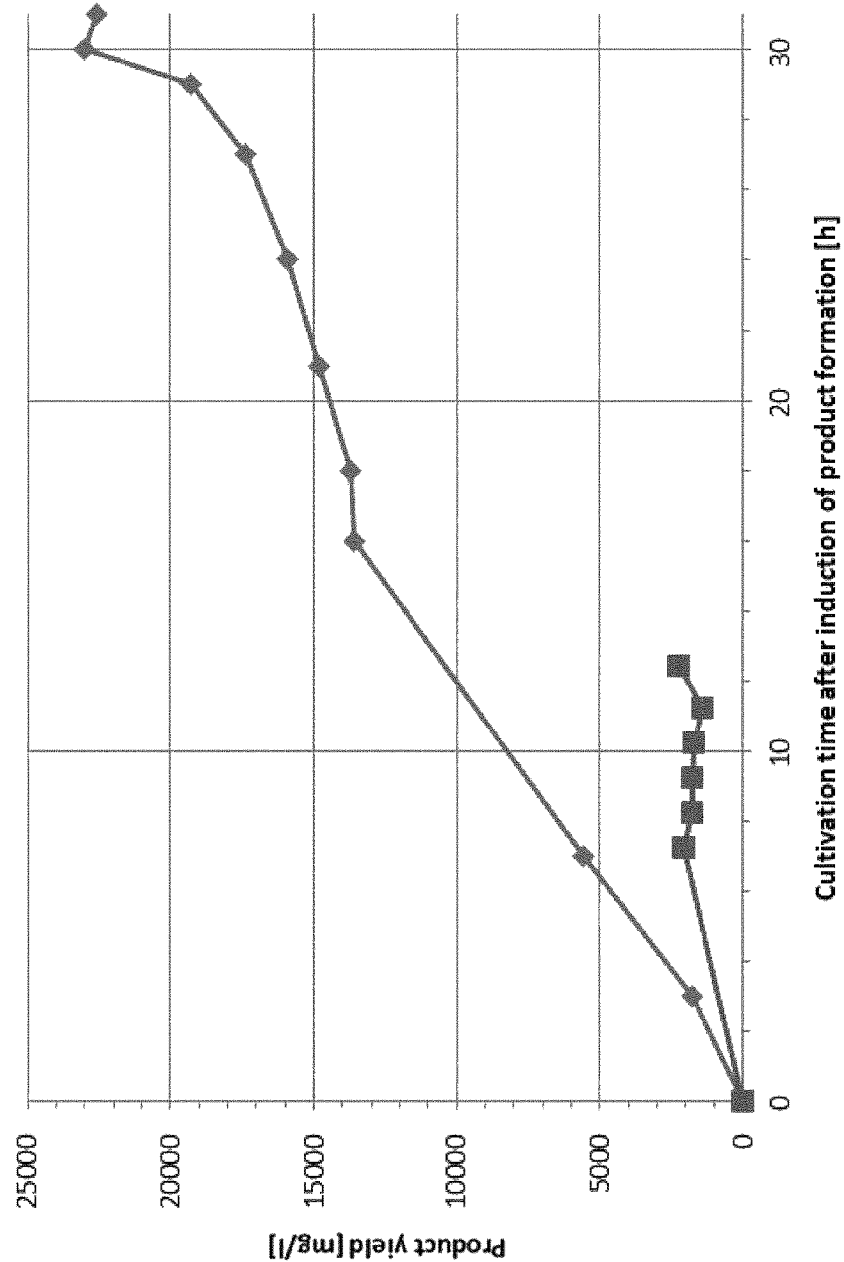
FIG. 8 Product yield comparison of auxotrophy cured strain CSPZ-6 (diamonds) and wild-type strain 66C5 (squares) on medium without amino acid supplementation.
Figure 9:
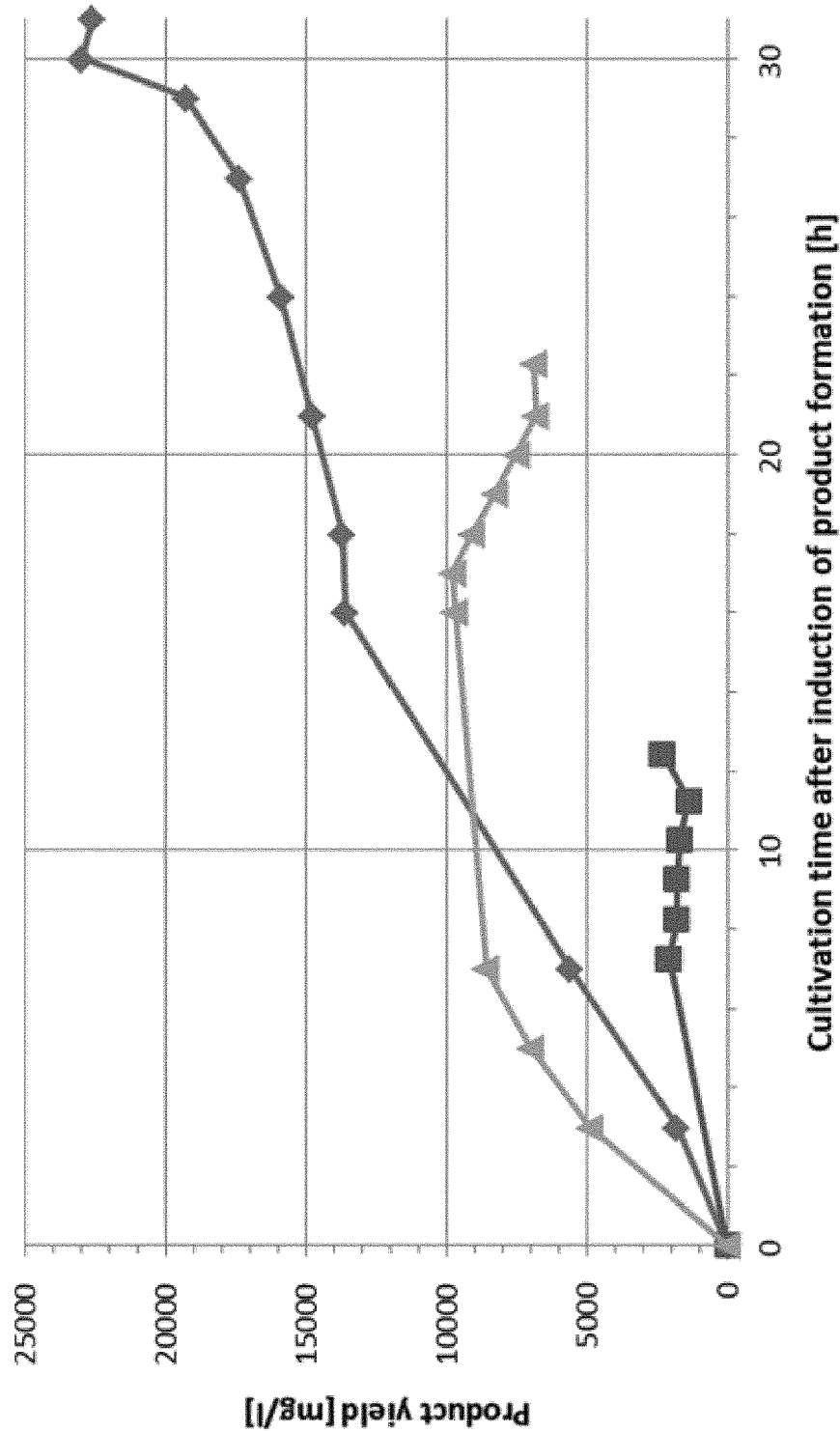
FIG. 9 Product yield comparison of auxotrophy cured strain CSPZ-6 (diamonds, normal temperature), wild-type strain 66C5 (squares, normal temperature), and wild-type strain 66C5 at elevated temperature (triangles) on medium without amino acid supplementation.

Because the growth of the wild-type strain 66C5 was way behind the growth of the auxotrophy cured strain CSPZ-6 when cultivated on the same chemically defined medium and under the same conditions, also product formation was much lower (see FIG. 8). While the auxotrophy cured strain finally obtained 22.6 g/L after 31 hours of expression the fermentation of wild-type strain 66C5 was terminated after 38 hours of cultivation due to stagnation of growth and consequently product yield was quantified at only 2.3 g/L. Also the specific productivity was lower (21.9 mg/OD vs. 71.1 mg/OD). The fermentation with the wild-type strain 66C5 was repeated with elevated temperatures for batch phase (37° C.) and fed-batch phase (30° C.), but product yield could only be improved to 6.9 g/L (see FIG. 9). The prototroph wild-type E. coli strain has significant deficiencies in direct comparison with the auxotrophy cured strain.

Summary:

The auxotrophy cured strain CSPZ-6 had a much better performance than a prototroph wild-type E. coli strain W3110 derivate on the same chemical defined fermentation medium without the supplementation of other amino acids than methionine. Therefore it is advantageous to cure E. coli strains from their amino acids auxotrophies in order to use a chemically defined minimal medium for cultivation and to profit from the advantages of using such a medium instead of using a prototrophic wild-type E. coli strain, such as for example MG1655 or W3110.

Example 7

Cultivation of Auxotrophy Cured Strain CSPZ-6 and the Prototrophic Wild-type Strain BL21 ΔpyrF Derivate on a Chemically Defined Medium To demonstrate that the auxotrophy cured strain CSPZ-6 has significant advantages over the prototrophic wild-type E. coli B strain BL21 (with deleted pyrF gene to fit to the antibiotic free selection system, named CSPZ-14) the growth and product formation within the same fermentation process has been explored.

The E. coli K12 strain CSPZ-6 (thi-1, ΔpyrF) and the E. coli B strain CSPZ-14 (=BL21 ΔpyrF derivate) were transformed by electroporation with the plasmid no. 5836 (see Example 2) to express a shortened tetranectin-apolipoprotein A-I fusion protein derivate. The transformed E. coli cells were first grown at 37° C. on agar plates. A colony picked from this plate was transferred to a 3 mL roller culture and grown at 37° C. to an optical density of 1-2 (measured at 578 nm). Then 1000 μL culture were mixed with 1000 μL sterile 86%-glycerol and immediately frozen at −80° C. for long time storage. The correct product expression of this clone was first verified in small scale shake flask experiments and analyzed with SDS-Page prior to the transfer to the 10 L fermenter.

Pre-cultivation:

For pre-cultivation a chemical defined medium (CDM) has been used:

NH4Cl 1.0 g/L, K2HPO4*3H2O 18.3 g/L, citrate 1.6 g/L, glycine 0.78 g/L, L-alanine 0.29 g/L, L-arginine 0.41 g/L, L-asparagine*H2O 0.37 g/L, L-aspartate 0.05 g/L, L-cysteine*HCl*H2O 0.05 g/L, L-histidine 0.05 g/L, L-isoleucine 0.31 g/L, L-leucine 0.38 g/L, L-lysine*HCl 0.40 g/L, L-methionine 0.27 g/L, L-phenylalanine 0.43 g/L, L-proline 0.36 g/L, L-serine 0.15 g/L, L-threonine 0.40 g/L, L-tryptophan 0.07 g/L, L-valine 0.33 g/L, L-tyrosine 0.51 g/L, L-glutamine 0.12 g/L, Na-L-glutamate*H2O 0.82 g/L, glucose*H2O 6.0 g/L, trace elements solution 0.5 mL/L, MgSO4*7H2O 0.86 g/L, thiamin*HCl 17.5 mg/L.

The trace elements solution contains FeSO4*7H2O 10.0 g/L, ZnSO4*7H2O 2.25 g/L, MnSO4*$H_2$O 2.13 g/L, H3BO3 0.50 g/L, (NH4)6Mo7O24*4H2O 0.3 g/L, CoCl2*6H2O 0.42 g/L, CuSO4*5H2O 1.0 g/L dissolved in 0.5M HCl.

For pre-cultivation 300 ml of CDM in a 1000 mL Erlenmeyer-flask with four baffles was inoculated with 0.9 mL out of a primary seed bank ampoule. The cultivation was performed on a rotary shaker for 8 hours at 32° C. and 170 rpm until an optical density (578 nm) of 4-9 was obtained. 100 g of this pre-cultivation was then transferred to the 10 L bioreactor to inoculate the batch medium.

Fermentation without Amino Acids L-leucine and L-proline (Experiment No. 10 and Experiment No. 11):

For fermentation in a 10 L Biostat C, DCU3 fermenter (Sartorius, Melsungen, Germany) the following batch medium was used:

$KH_2PO_4$ 1.58 g/L, $(NH_4)_2HPO_4$ 7.47 g/L, K2HPO4*3H2O 13.32 g/L, citrate 2.07 g/L, L-methionine 1.22 g/L, NaHCO$_3$ 0.82 g/L, trace elements solution 7.3 mL/L, MgSO$_4$*7H$_2$O 0.99 g/L, thiamine*HCl 20.9 mg/L, glucose*H$_2$O 29.3 g/L, biotin 0.2 mg/L, 1.2 mL/L Synperonic 10% anti foam agent.

The trace elements solution contains FeSO4*7H2O 10 g/L, ZnSO4*7H2O 2.25 g/L, MnSO4*H2O 2.13 g/L, CuSO4*5H2O 1.0 g/L, CoCl2*6H2O 0.42 g/L, (NH4)6Mo7O24*4H2O 0.3 g/L, H3BO3 0.50 g/L solubilized in 0.5M HCl solution.

The feed 1 solution contained 700 g/L glucose*H2O, 7.4 g/L MgSO$_4$*7H$_2$O and 0.1 g/L FeSO4*7H2O.

Feed 2 comprises KH$_2$PO$_4$ 52.7 g/L, K2HPO4*3H2O 139.9 g/L and (NH4)2HPO4 66.0 g/L.

All components were dissolved in deionized water.

The alkaline solution for pH regulation was an aqueous 12.5% (w/v) NH$_3$ solution supplemented with 11.25 g/L L-methionine.

Starting with 4.2 L sterile batch medium plus 100 mL inoculum from the pre cultivation the batch fermentation was performed at 31° C., pH 6.9±0.2, 800 mbar back pressure and an initial aeration rate of 10 L/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 25° C. and 15 minutes later the fermentation entered the fed-batch mode with the start of both feeds (60 and 14 g/h respectively). The rate of feed 2 is kept constant, while the rate of feed 1 is increased stepwise with a predefined feeding profile from 60 to finally 160 g/h within 7 hours. When carbon dioxide off gas concentration leveled above 2% the aeration rate was constantly increased from 10 to 20 L/min within 5 hours. The expression of recombinant tetranectin-apolipoprotein A-I fusion protein was induced by the addition of 2.4 g IPTG at an optical density of approx. 150. At the end of fermentation the within the cytoplasm soluble expressed tetranectin-apolipoprotein A-I is transferred to insoluble protein aggregates, the so called inclusion bodies, with a heat step where the whole culture broth in the fermenter is heated to 50° C. for 1 hour before harvest (see e.g. EP-B 1 486 571). Thereafter, the content of the fermenter was centrifuged with a flow-through centrifuge (13,000 rpm, 13 L/h) and the harvested biomass was stored at −20° C. until further processing. The synthesized tetranectin-apolipoprotein A-I fusion proteins were found exclusively in the insoluble cell debris fraction in the form of insoluble protein aggregates, so-called inclusion bodies (IBs).

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OE_{target}$=5) are suspended in 5 mL PBS buffer and disrupted via sonication on ice. Then 100 µL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 µL and to each pellet (=insoluble) fraction 400 µL of SDS sample buffer (Laemmli, U. K., Nature 227 (1970) 680-685) are added. Samples are heated for 15 minutes at 95° C. under intense mixing to solubilize and reduce all proteins in the samples. After cooling to room temperature 5 µL of each sample are transferred to a 4-20% TGX Criterion Stain Free polyacrylamide gel (Bio-Rad). Additionally 5 µL molecular weight standard (Precision Plus Protein Standard, Bio-Rad) and 3 amounts (0.3 µL, 0.6 µL and 0.9 µL) quantification standard with known product protein concentration (0.1 µg/µL) are positioned on the gel.

The electrophoresis was run for 60 min. at 200 V and thereafter the gel was transferred the GelDOC EZ Imager (Bio-Rad) and processed for 5 min. with UV radiation. Gel images were analyzed using Image Lab analysis software (Bio-Rad). With the three standards a linear regression curve was calculated with a coefficient of >0.99 and thereof the concentrations of target protein in the original sample was calculated.

The activity of the purified and lipidated shortened TN-ApoA1 was measured in an eight day radioactive efflux assay. Cells (THP-1) were differentiated by PMA (phorbol myristate acetate) to macrophages. These cells were loaded with acetylated LDL and $^3$H-labeled cholesterol. The supernatant was discarded and cells were incubated for 5 hours with equilibration medium to remove non-specifically bound cholesterol. The lipidated shortened TN-ApoA1 was added which enabled the export of the $^3$H-labeled cholesterol out of the cells during the following 18 hours. Radioactivity was measured in the supernatant and in the cell lysate.

Results:

The above mentioned fermentation process was used to express a shortened tetranectin-apolipoprotein A-I fusion protein in the auxotrophy cured strain CSPZ-6 and in the prototrophic strain CSPZ-14 representing the E. coli B wild-type strain BL21. Both strains do not need the feeding of the amino acids L-leucine and L-proline which where consequently excluded from the medium and feeds. This reduces cost of goods for the process.

Figure 10:
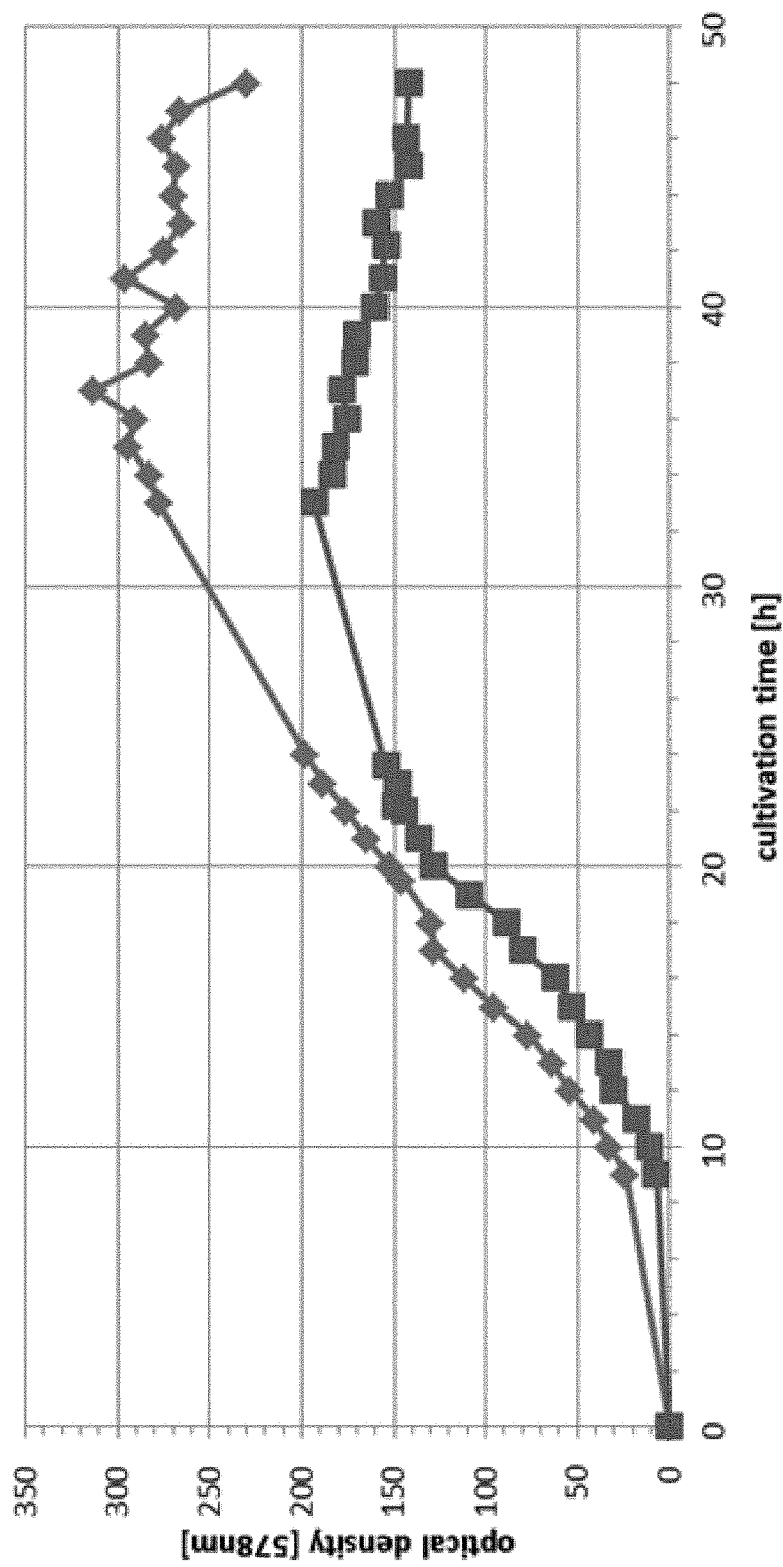
FIG. 10 Growth comparison of auxotrophy cured strain CSPZ-6 (diamonds) and wild-type strain BL21 on medium without amino acid supplementation.

Surprisingly the wild-type strain and BL21 derivate CSPZ-14, despite being prototrophic and the fermentation was inoculated with an equal amount of cells, grew significantly slower from the start when compared to the auxotrophy cured strain CSPZ-6 on the same chemically defined medium and under the same cultivation conditions (see FIG. 10). As a consequence the glucose feeding started 1.2 hours later, but the increase of the feed rate followed the same profile as in the comparative fermentation. The final optical densities differ greatly between both strains. While the auxotrophy cured strain reached an optical density of 266 before the final heat step the optical density of the wild-type strain was decreasing form a maximum at hour 33 to only 143 at the end of the fermentation (hour 47).

Figure 11:
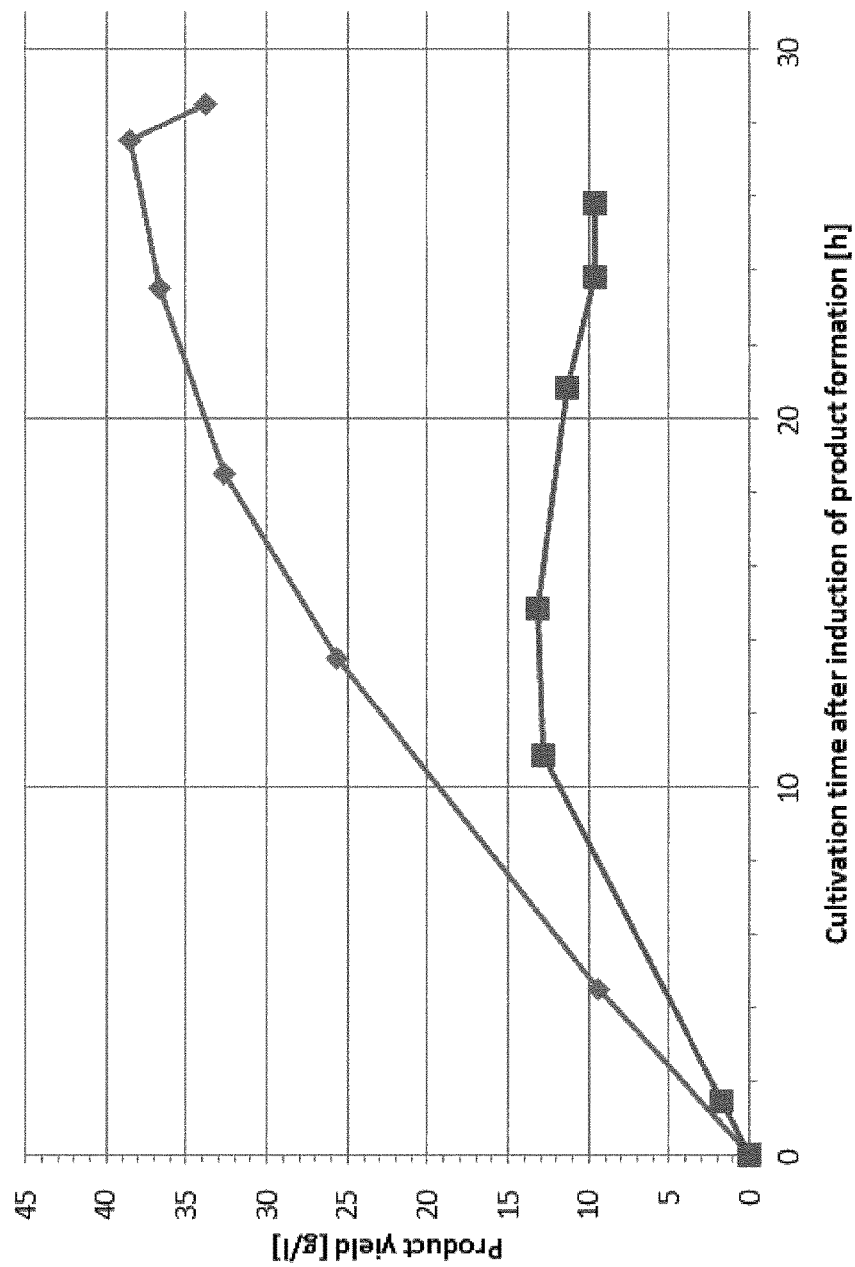
FIG. 11 Product yield comparison of auxotrophy cured strain CSPZ-6 (diamonds) and wild-type strain BL21 (squares) on medium without amino acid supplementation.

Product formation was induced by the addition of 2.4 g IPTG at an optical density of approx. 150 in both cultivations. Due to the reduced growth of the strain CSPZ-14 this OD was reached at hour 22.2 in comparison to hour 19.5 with strain CSPZ-6 when cultivated on the same chemically defined medium and under the same conditions. Despite that product formation rate of CSPZ-14 was significant lower and therefore the final yield reached only 9.6 g/L after 23 hours of expression (see FIG. 11). In comparison to that the auxotrophy cured strain yielded in 33.8 g/L fusion protein after 24 hours of induced expression. Also the specific productivity was lower (67.1 mg/OD vs. 135.7 mg/OD). The prototroph wild-type E. coli strain has significant deficits in direct comparison with the auxotrophy cured strain.

Summary:

The auxotrophy cured strain CSPZ-6 had a much better performance than a prototroph wild-type *E. coli* strain CSPZ-14 (BL21 ΔpyrF derivate) on the same chemical defined fermentation medium without the supplementation of other amino acids than methionine. Therefore it is advantageous to cure *E. coli* strains from their amino acids auxotrophies in order to culture them on chemically defined minimal medium and profit from the advantages of using such a medium instead of using a prototrophic wild-type *E. coli* strain, such as for example MG1655, W3110 or BL21.

Example 8

Cultivation of Auxotrophy Cured Strain CSPZ-6 and the Prototrophic Wild-type Strain MG1655 on a Chemically Defined Medium To demonstrate that the auxotrophy cured strain CSPZ-6 has significant advantages over the prototrophic wild-type *E. coli* K12 strain MG1655 (with deleted pyrF gene to fit to the antibiotic free selection system, named CSPZ-9) growth and IgA-protease product formation within the same fermentation process between the two strains has been explored.

The *E. coli* K12 strains CSPZ-6 (thi-1, ΔpyrF) and CSPZ-9 (=MG1655 ΔpyrF derivate) were transformed by electroporation with the plasmid 3036 to express IgA-protease. The transformed *E. coli* cells were first grown at 37° C. on agar plates. A colony picked from this plate was transferred to a 3 mL roller culture and grown at 37° C. to an optical density of 1-2 (measured at 578 nm). Then 1000 µL culture were mixed with 1000 µL sterile 86%-glycerol and immediately frozen at −80° C. for long time storage. The correct product expression of this clone was first verified in small scale shake flask experiments and analyzed with SDS-Page prior to the transfer to the 10 L fermenter.

Pre-cultivation:

For pre-cultivation a chemical defined medium (CDM) has been used:

NH4Cl 1.0 g/L, K2HPO4*3H2O 18.3 g/L, citrate 1.6 g/L, glycine 0.78 g/L, L-alanine 0.29 g/L, L-arginine 0.41 g/L, L-asparagine*H2O 0.37 g/L, L-aspartate 0.05 g/L, L-cysteine*HCl*H2O 0.05 g/L, L-histidine 0.05 g/L, L-isoleucine 0.31 g/L, L-leucine 0.38 g/L, L-lysine*HCl 0.40 g/L, L-methionine 0.27 g/L, L-phenylalanine 0.43 g/L, L-proline 0.36 g/L, L-serine 0.15 g/L, L-threonine 0.40 g/L, L-tryptophan 0.07 g/L, L-valine 0.33 g/L, L-tyrosine 0.51 g/L, L-glutamine 0.12 g/L, Na-glutamate*H2O 0.82 g/L, glucose*H2O 6.0 g/L, trace elements solution 0.5 mL/L, MgSO4*7H2O 0.86 g/L, thiamin*HCl 17.5 mg/L.

The trace elements solution contains FeSO4*7H2O 10.0 g/L, ZnSO4*7H2O 2.25 g/L, MnSO4*H2O 2.13 g/L, H3BO3 0.50 g/L, (NH4)6Mo7O24*4H2O 0.3 g/L, CoCl2*6H2O 0.42 g/L, CuSO4*5H2O 1.0 g/L dissolved in 0.5M HCl.

For pre-cultivation 220 ml of CDM in a 1000 mL Erlenmeyer-flask with four baffles was inoculated with 0.9 mL out of a primary seed bank ampoule. The cultivation was performed on a rotary shaker for 8 hours at 37° C. and 170 rpm until an optical density (578 nm) of 10-12 was obtained. To inoculate the batch medium of the 10 L bioreactor with equal amount of cells, the inoculum volume was calculated with $V_{inoc.}=100$ mL*5/OD$_{PC}$ and is therefore dependent on the optical density of the pre cultivation.

Fermentation without Amino Acids L-leucine and L-proline (Experiment No. 12 and Experiment No. 13):

For fermentation in a 10 L Biostat C, DCU3 fermenter (Sartorius, Melsungen, Germany) the following batch medium was used:

KH2PO4 1.58 g/L, (NH4)2HPO4 7.47 g/L, K2HPO4*3H2O 13.32 g/L, citrate 2.07 g/L, L-methionine 1.22 g/L, NaHCO3 0.82 g/L, trace elements solution 7.3 mL/L, MgSO4*7H2O 0.99 g/L, thiamine*HCl 20.9 mg/L, glucose*H2O 29.3 g/L, biotin 0.2 mg/L, 1.2 mL/L Synperonic 10% anti foam agent.

The trace elements solution contains FeSO4*7H2O 10 g/L, ZnSO4*7H2O 2.25 g/L, MnSO4*H2O 2.13 g/L, CuSO4*5H2O 1.0 g/L, CoCl2*6H2O 0.42 g/L, (NH4)6Mo7O24*4H2O 0.3 g/L, H3BO3 0.50 g/L solubilized in 0.5 M HCl solution.

The feed 1 solution contained 700 g/L glucose*H2O, 7.4 g/L MgSO4*7H2O and 0.1 g/L FeSO4*7H2O.

Feed 2 comprises KH2PO4 52.7 g/L, K2HPO4*3H2O 139.9 g/L and (NH4)2HPO4 66.0 g/L.

All components were dissolved in deionized water.

The alkaline solution for pH regulation was an aqueous 12.5% (w/v) NH3 solution supplemented with 11.25 g/L L-methionine.

Starting with 4.2 L sterile batch medium plus the respective inoculum volume the batch fermentation was performed at 31° C., pH 6.9±0.2, 800 mbar back pressure and an initial aeration rate of 10 L/min. The relative value of dissolved oxygen (pO2) was kept at 50% throughout the fermentation by increasing the stirrer speed up to 1500 rpm. After the initially supplemented glucose was depleted, indicated by a steep increase in dissolved oxygen values, the temperature was shifted to 25° C. and 15 minutes later the fermentation entered the fed-batch mode with the start of both feeds (60 and 14 g/h respectively). The rate of feed 2 is kept constant, while the rate of feed 1 is increased stepwise with a predefined feeding profile from 60 to finally 160 g/h within 7 hours. When carbon dioxide off gas concentration leveled above 2% the aeration rate was constantly increased from 10 to 20 L/min within 5 hours. The expression of recombinant IgA-protease was induced by the addition of 2.4 g IPTG at an optical density of approx. 150. The fermentation is conducted up to 48 hours despite there is no significant decrease in optical density. In the end the culture broth is cooled to 4-8° C. and stored overnight in the fermenter vessel. The content of the fermenter was centrifuged the next day with a flow-through centrifuge (13,000 rpm, 13 L/h) and the harvested biomass was stored at −20° C. until further processing. The synthesized IgA-protease is found exclusively in the insoluble cell debris fraction in the form of insoluble protein aggregates the so-called inclusion bodies (IBs).

Analysis of Product Formation:

Samples drawn from the fermenter, one prior to induction and the others at dedicated time points after induction of protein expression are analyzed with SDS-Polyacrylamide gel electrophoresis. From every sample the same amount of cells ($OE_{target}$=10) are suspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 100 μL and to each pellet (=insoluble) fraction 200 μL of SDS sample buffer (Laemmli, U. K., Nature 227 (1970) 680-685) are added. Samples are heated for 15 minutes at 95° C. under intense mixing to solubilize and reduce all proteins in the samples. After cooling to room temperature 5 μL of each sample are transferred to a 4-20% TGX Criterion Stain Free polyacrylamide gel (Bio-Rad). Additionally 5 μL molecular weight standard (Precision Plus Protein Standard, Bio-Rad) and 3 amounts (0.3 μL, 0.6 μL and 0.9 μL) quantification standard with known product protein concentration (0.15 μg/μL) are positioned on the gel.

The electrophoresis was run for 60 min. at 200 V and thereafter the gel was transferred the GelDOC EZ Imager (Bio-Rad) and processed for 5 min. with UV radiation. Gel images were analyzed using Image Lab analysis software (Bio-Rad). With the three standards a linear regression curve was calculated with a coefficient of >0.99 and thereof the concentrations of target protein in the original sample was calculated.

The activity of the refolded and purified IgA-protease was tested with the molecule tetranectin-apolipoprotein A-I fusion polypeptides as described above which is a precursor polypeptide from which the tetranectin-apolipoprotein A-I fusion polypeptides was released by enzymatic cleavage in vitro using this IgA protease. Cleavage activity was in the expected range.

Results:

The above mentioned fermentation process was used to express IgA-Protease protein in the auxotrophy cured strain CSPZ-6 and in the prototrophic strain CSPZ-9 representing the *E. coli* K12 wild-type strain MG1655. Both strains do not need the feeding of the amino acids L-leucine and L-proline which where consequently excluded from the medium and feeds. This dramatically reduces cost of goods for the process.

Figure 12:
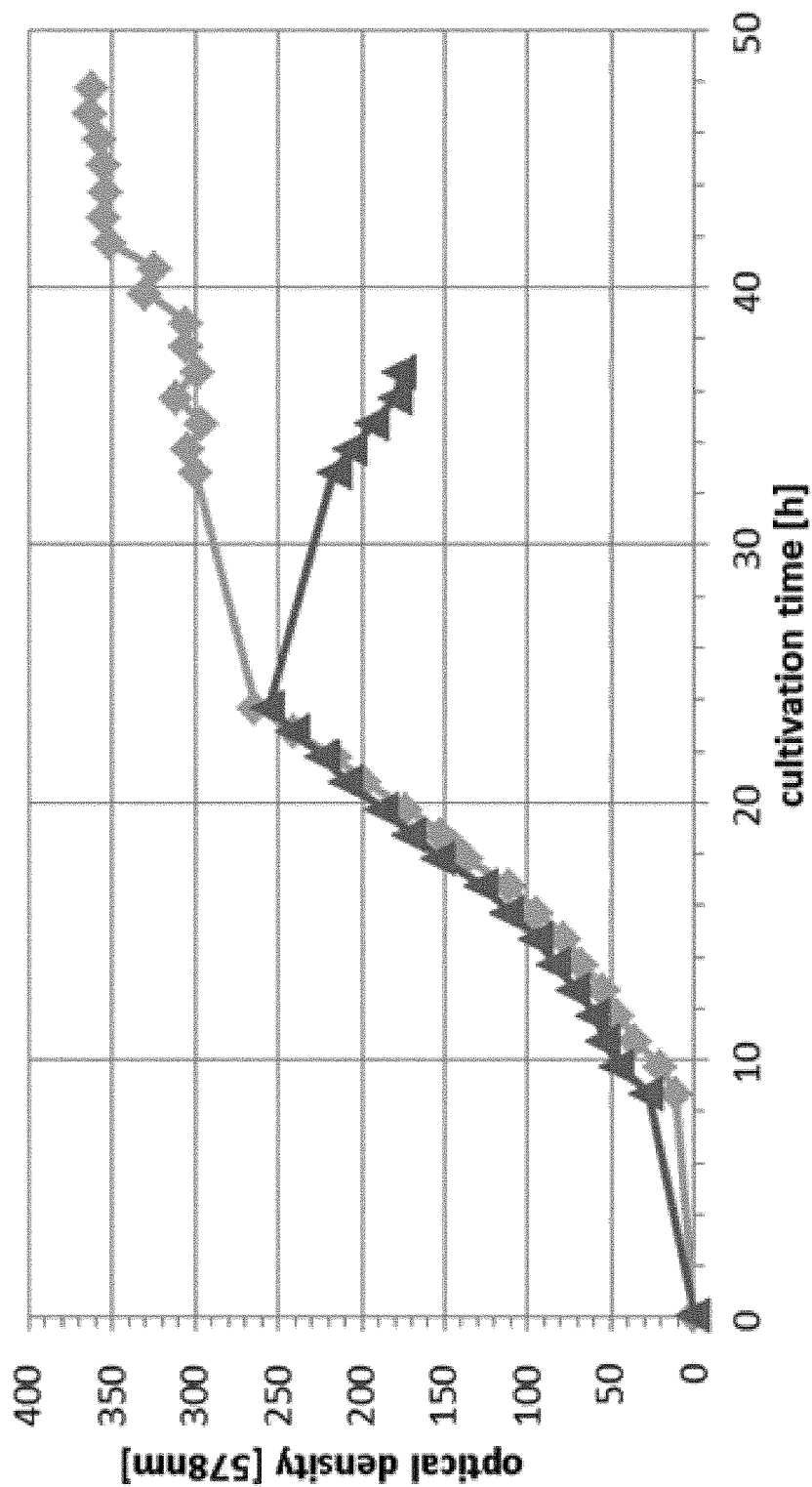
FIG. 12 Growth comparison of auxotrophy cured strain CSPZ-6 (diamonds) and wild-type strain MG1655 derivate (triangles).

The wild-type strain and MG1655 derivate CSPZ-9 showed a faster growth in the beginning of the fermentation when compared to the auxotrophy cured strain CSPZ-6 on the same chemically defined medium and under the same cultivation conditions. 24 hours after inoculation the optical densities were almost the same. But thereafter the optical density of both strains was surprisingly different. The growth of strain CSPZ-9 had significantly slowed down after 30 hours of cultivation and as a consequence of the continuous feeding of feed 1 the glucose concentration in the medium increased to 16 g/L. Therefore the fermentation was terminated after 37 hours of cultivation. Metabolite analysis revealed a significant increase in concentrations of ammonia, glutamate, iron, magnesium and acetate in the medium due to the significant decrease in growth rate. The final optical densities differ greatly between both strains. While the cured strain reached 362 the optical density of the wild-type strain was decreasing form a maximum at hour 24 of 256 to only 177 at the end of the fermentation (hour 37) (see FIG. 12).

Figure 13:
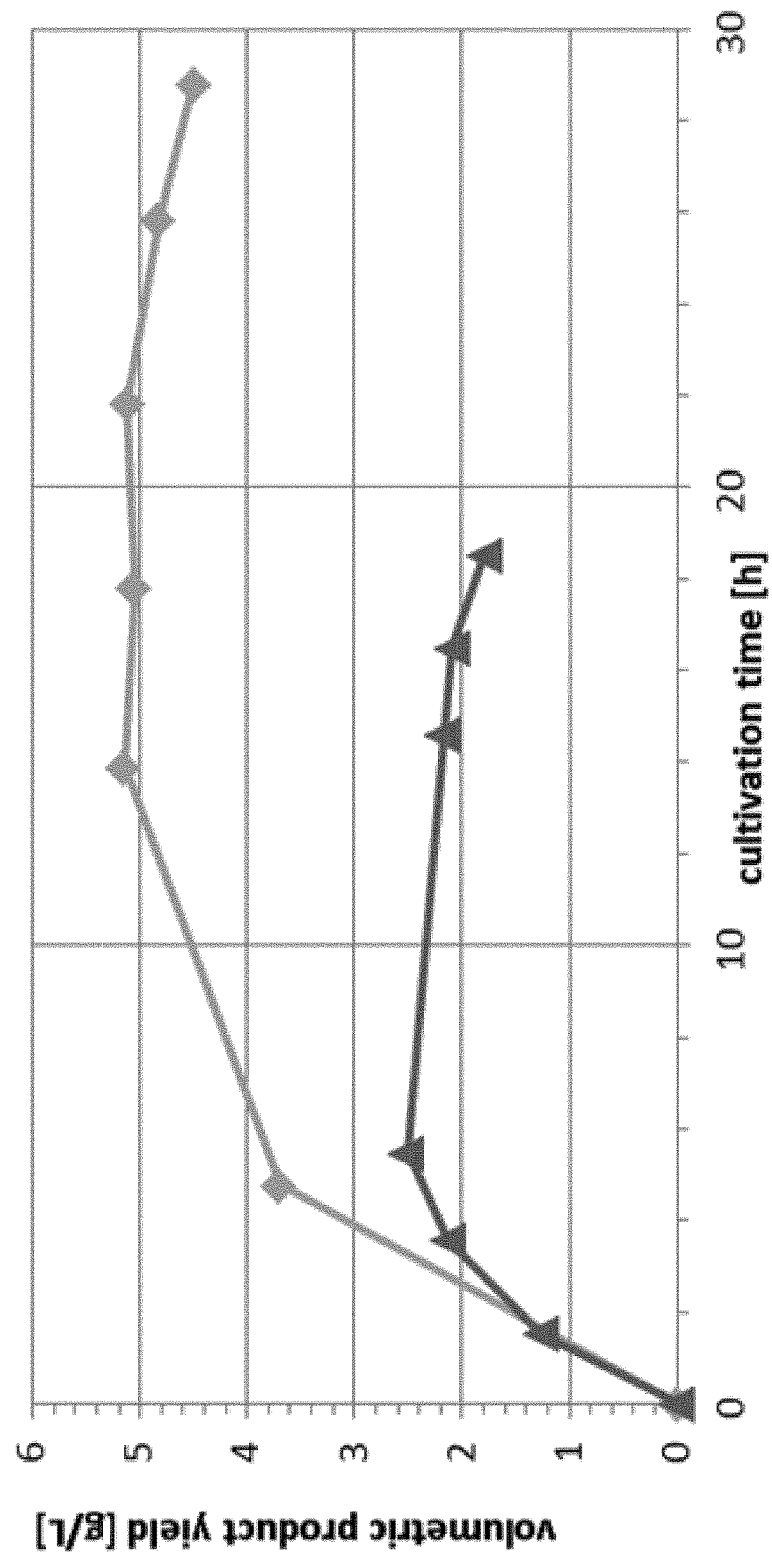
FIG. 13 Product yield comparison of auxotrophy cured strain CSPZ-6 (diamonds) and wild-type strain MG1655 derivate (triangles).

After the induction of protein expression with the addition of 2.4 g IPTG at an optical density of approx. 150 significantly more IgA-9 rotease is produced with strain CSPZ-6 when compared to the wild-type strain CSPZ-9 (see FIG. 13).

Summary:

The auxotrophy cured strain CSPZ-6 showed improved growth characteristics compared to the prototroph wild-type *E. coli* strain CSPZ-9 (MG1655 ΔpyrF derivate) on the same chemical defined fermentation medium without the supplementation of other amino acids. Therefore it is useful to cure highly productive *E. coli* strains from its amino acids auxotrophies in order to be able to culture them on chemically defined minimal medium and profit from the advantages of using such a medium and instead of using a prototrophic wild-type *E. coli* strain derivate from MG1655, W3110 or BL21.

---

The invention claimed is:

1. A method for increasing the titer of a polypeptide produced in a prokaryotic cell, comprising the following steps:
   providing a parent amino acid auxotrophic prokaryotic cell that cannot synthesize at least one amino acid due to a mutation or deletion within the gene locus comprising the structural gene encoding a protein of the corresponding amino acid biosynthetic pathway;
   producing an auxotrophy cured prokaryotic cell by introducing into the genome of the parent amino acid auxotrophic prokaryotic cell a nucleic acid curing the amino acid auxotrophy of the parent prokaryotic cell, wherein the nucleic acid encodes the protein of the corresponding amino acid biosynthetic pathway;
   introducing into said auxotrophy cured prokaryotic cell one or more nucleic acids encoding the polypeptide; and
   cultivating the auxotrophy cured prokaryotic cell comprising one or more nucleic acids encoding the polypeptide in a chemically defined minimal growth medium and recovering the polypeptide from the prokaryotic cell or the periplasm of the prokaryotic cell or from the medium.

2. The method according to claim 1, characterized in that the cultivation of the auxotrophy cured prokaryotic cell requires supplementation of one or two or three or four amino acids less to the growth medium than required for the cultivation of the parent non-auxotrophy cured prokaryotic cell.

3. The method according to claim 1, characterized in that the auxotrophy cured prokaryotic cell has at least one further amino acid auxotrophy.

4. The method according to claim 1, characterized in that the amino acid corresponding to the auxotrophy that has been cured in the auxotrophy cured prokaryotic cell is not added during the cultivation.

5. The method according to claim 1, characterized in that the cultivation is in the absence of the amino acid corresponding to the auxotrophy that has been cured in the auxotrophy cured prokaryotic cell.

6. The method according to claim 1, characterized in that the prokaryotic cell is an *E. coli* cell.

7. The method according to claim 1, characterized in that the polypeptide is a full length antibody chain, a single chain antibody, a single domain antibody, a scFv, a scFab, or a conjugate of a scFV or scFab with a non-antibody polypeptide.

8. The method according to claim 7, characterized in that the polypeptide is a conjugate of a scFv or scFab with a cytotoxic agent.

9. The method according to claim 2, characterized in that the auxotrophy cured prokaryotic cell has at least one further amino acid auxotrophy.

10. The method according to claim 2, characterized in that the amino acid corresponding to the auxotrophy that has been cured in the auxotrophy cured prokaryotic cell is not added during the cultivation.

11. The method according to claim 2, characterized in that the cultivation is in the absence of the amino acid corresponding to the auxotrophy that has been cured in the auxotrophy cured prokaryotic cell.

12. The method according to claim 2, characterized in that the prokaryotic cell is an *E. coli* cell.

13. The method according to claim 2, characterized in that the polypeptide is a full length antibody chain, a single chain antibody, a single domain antibody, a scFv, a scFab, or a conjugate of a scFV or scFab with a non-antibody polypeptide.

14. The method according to claim 13, characterized in that the polypeptide is a conjugate of a scFv or scFab with a cytotoxic agent.

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Cys Asp Leu Pro Gln Thr His Ser Leu
1               5

<210> SEQ ID NO 2
<211> LENGTH: 6
<212> TYPE: PRT
<213> ORGANISM: Artificial Sequence
<220> FEATURE:
<223> OTHER INFORMATION: hexa-histidine tag

<400> SEQUENCE: 2

His His His His His His
1               5
```

<210> SEQ ID NO 3
<211> LENGTH: 7
<212> TYPE: PRT
<213> ORGANISM: Homo sapiens

<400> SEQUENCE: 3

Val Val Ala Pro Pro Ala Pro
1               5

<210> SEQ ID NO 4
<211> LENGTH: 283
<212> TYPE: PRT
<213> ORGANISM: Artificial Sequence
<220> FEATURE:
<223> OTHER INFORMATION: tetranectin-apolipoprotein A1 fusion protein

<400> SEQUENCE: 4

Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val Asp Glu Pro Pro Gln Ser Pro Trp
        35                  40                  45

Asp Arg Val Lys Asp Leu Ala Thr Val Tyr Val Asp Val Leu Lys Asp
    50                  55                  60

Ser Gly Arg Asp Tyr Val Ser Gln Phe Glu Gly Ser Ala Leu Gly Lys
65                  70                  75                  80

Gln Leu Asn Leu Lys Leu Leu Asp Asn Trp Asp Ser Val Thr Ser Thr
                85                  90                  95

Phe Ser Lys Leu Arg Glu Gln Leu Gly Pro Val Thr Gln Glu Phe Trp
            100                 105                 110

Asp Asn Leu Glu Lys Glu Thr Glu Gly Leu Arg Gln Glu Met Ser Lys
        115                 120                 125

Asp Leu Glu Glu Val Lys Ala Lys Val Gln Pro Tyr Leu Asp Asp Phe
    130                 135                 140

Gln Lys Lys Trp Gln Glu Glu Met Glu Leu Tyr Arg Gln Lys Val Glu
145                 150                 155                 160

Pro Leu Arg Ala Glu Leu Gln Glu Gly Ala Arg Gln Lys Leu His Glu
                165                 170                 175

Leu Gln Glu Lys Leu Ser Pro Leu Gly Glu Glu Met Arg Asp Arg Ala
            180                 185                 190

Arg Ala His Val Asp Ala Leu Arg Thr His Leu Ala Pro Tyr Ser Asp
        195                 200                 205

Glu Leu Arg Gln Arg Leu Ala Ala Arg Leu Glu Ala Leu Lys Glu Asn
    210                 215                 220

Gly Gly Ala Arg Leu Ala Glu Tyr His Ala Lys Ala Thr Glu His Leu
225                 230                 235                 240

Ser Thr Leu Ser Glu Lys Ala Lys Pro Ala Leu Glu Asp Leu Arg Gln
                245                 250                 255

Gly Leu Leu Pro Val Leu Glu Ser Phe Lys Val Ser Phe Leu Ser Ala
            260                 265                 270

Leu Glu Glu Tyr Thr Lys Lys Leu Asn Thr Gln
        275                 280

<210> SEQ ID NO 5
<211> LENGTH: 285
<212> TYPE: PRT

<213> ORGANISM: Artificial Sequence
<220> FEATURE:
<223> OTHER INFORMATION: Tetranectin-apolipoprotein A-I (1)

<400> SEQUENCE: 5

```
Ala Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
        275                 280                 285
```

<210> SEQ ID NO 6
<211> LENGTH: 284
<212> TYPE: PRT
<213> ORGANISM: Artificial Sequence
<220> FEATURE:
<223> OTHER INFORMATION: shortened tetranectin-apolipoprotein A1 fusion protein

<400> SEQUENCE: 6

```
Pro Ile Val Asn Ala Lys Lys Asp Val Val Asn Thr Lys Met Phe Glu
1               5                   10                  15

Glu Leu Lys Ser Arg Leu Asp Thr Leu Ala Gln Glu Val Ala Leu Leu
            20                  25                  30

Lys Glu Gln Gln Ala Leu Gln Thr Val Asp Glu Pro Pro Gln Ser Pro
        35                  40                  45
```

-continued

```
Trp Asp Arg Val Lys Asp Leu Ala Thr Val Tyr Val Asp Val Leu Lys
     50                  55                  60

Asp Ser Gly Arg Asp Tyr Val Ser Gln Phe Glu Gly Ser Ala Leu Gly
 65              70                  75                  80

Lys Gln Leu Asn Leu Lys Leu Leu Asp Asn Trp Asp Ser Val Thr Ser
             85                  90                  95

Thr Phe Ser Lys Leu Arg Glu Gln Leu Gly Pro Val Thr Gln Glu Phe
            100                 105                 110

Trp Asp Asn Leu Glu Lys Glu Thr Glu Gly Leu Arg Gln Glu Met Ser
            115                 120                 125

Lys Asp Leu Glu Glu Val Lys Ala Lys Val Gln Pro Tyr Leu Asp Asp
            130                 135                 140

Phe Gln Lys Lys Trp Gln Glu Glu Met Glu Leu Tyr Arg Gln Lys Val
145                 150                 155                 160

Glu Pro Leu Arg Ala Glu Leu Gln Glu Gly Ala Arg Gln Lys Leu His
            165                 170                 175

Glu Leu Gln Glu Lys Leu Ser Pro Leu Gly Glu Glu Met Arg Asp Arg
            180                 185                 190

Ala Arg Ala His Val Asp Ala Leu Arg Thr His Leu Ala Pro Tyr Ser
            195                 200                 205

Asp Glu Leu Arg Gln Arg Leu Ala Ala Arg Leu Glu Ala Leu Lys Glu
            210                 215                 220

Asn Gly Gly Ala Arg Leu Ala Glu Tyr His Ala Lys Ala Thr Glu His
225                 230                 235                 240

Leu Ser Thr Leu Ser Glu Lys Ala Lys Pro Ala Leu Glu Asp Leu Arg
            245                 250                 255

Gln Gly Leu Leu Pro Val Leu Glu Ser Phe Lys Val Ser Phe Leu Ser
            260                 265                 270

Ala Leu Glu Glu Tyr Thr Lys Lys Leu Asn Thr Gln
            275                 280
```